(12) United States Patent
Kinch et al.

(10) Patent No.: US 7,604,799 B2
(45) Date of Patent: Oct. 20, 2009

(54) EPHA4 ANTIBODIES

(75) Inventors: Michael S. Kinch, Laytonsville, MD (US); Kelly Carles-Kinch, Laytsonville, MD (US)

(73) Assignee: Medimmune, LLC, Gaithersburg, MD (US)

( * ) Notice: Subject to any disclaimer, the term of this patent is extended or adjusted under 35 U.S.C. 154(b) by 17 days.

(21) Appl. No.: 10/863,729

(22) Filed: Jun. 7, 2004

(65) Prior Publication Data

US 2005/0013819 A1 Jan. 20, 2005

Related U.S. Application Data

(60) Provisional application No. 60/476,909, filed on Jun. 6, 2003, provisional application No. 60/503,356, filed on Sep. 16, 2003.

(51) Int. Cl.
A61K 39/395 (2006.01)
C07K 16/30 (2006.01)
(52) U.S. Cl. .............. 424/141.1; 424/143.1; 424/174.1; 530/387.1; 530/388.1; 530/388.8
(58) Field of Classification Search ............... 530/387.1
See application file for complete search history.

(56) References Cited

U.S. PATENT DOCUMENTS

| 5,322,798 | A | 6/1994 | Sadowski |
| 5,341,215 | A | 8/1994 | Seher |
| 6,268,125 | B1 | 7/2001 | Perkins |
| 6,289,286 | B1 | 9/2001 | Andersson et al. |
| 6,373,577 | B1 | 4/2002 | Brauer et al. |
| 6,984,720 | B1 * | 1/2006 | Korman et al. ......... 530/388.22 |
| 2003/0224374 | A1 | 12/2003 | Dai et al. |
| 2004/0028685 | A1 | 2/2004 | Kinch et al. |
| 2004/0180823 | A1 | 9/2004 | Pasquale et al. |

FOREIGN PATENT DOCUMENTS

| WO | WO 99/54440 | 10/1999 |
| WO | WO 01/00678 A1 * | 1/2001 |
| WO | WO 01/94629 | 12/2001 |

OTHER PUBLICATIONS

Freshney (Culture of Animal Cells, A Manual of Basic Technique, Alan R. Liss, Inc., 1983, New York, p4).*
Dermer (Bio/Technology, 1994, 12:320)*
Kipps et al (J Exp Med, 1988, 167:840-852).*
Easty et al (Int J Cancer, 1997, 71:1061-1065, IDS).*
iHOP, EphA4, 2 pages.*
Rudikoff et al, PNAS, USA, 1982, 79: 1979-1983.*
Panka et al (Proc Natl Acad Sci, 1988, 85:3080-3084).*
MacCallum et al (J Mol Biology, 1996, 262:732-745).*
Easty et al (Int J Cancer, 1997, 71:1061-1065, IDS).*
iHOP, p.1.*
Freitas et al, Dev Genes Evol, 2004, 214:466-472.*
Kultima et al (BMC Bioinformatics, 2006, 7:475, internet pp. 1-27).*
Sambrook et al. (Molecular Cloning, 2nd edition, Cold Spring Harbor Press, 1989, p. 18.47).*
Invitrogen™ product information sheet for protein standards and ladders, p. 1-4.*
Wada et al (Developmental Biology, 1998, 202:244-252).*
U.S. Appl. No. 60/622,711, filed Oct. 27, 2004, Kinch.
U.S. Appl. No. 60/503,356, filed Sep. 16, 2003, Carles-Kinch et al.
U.S. Appl. No. 60/476,909, filed Jun. 6, 2003, Carles-Kinch et al.
U.S. Appl. No. 09/952,560, filed Sep. 12, 2001, Kilpatrick et al.
Ashida et al., 2004, "Molecular features of the transition from prostatic intraepithelial neoplasia (PIN) to prostate cancer: genome-wide gene-expression profiles of prostate cancers and PINs," Cancer Res. 64(17):5963-5972.
Burridge et al., 1996, "Focal adhesions, contractility, and signaling," Annu. Rev. Cell Dev. Biol. 12:463-518.
Cance et al., 1995, "Protein kinases in human breast cancer," Breast Cancer Res. Treat. 35(1):105-114.
Chaiken et al., 1992, "Analysis of macromolecular interactions using immobilized ligands," Anal. Biochem. 201(2):197-210.
Cheng et al., 2002, "The ephrins and Eph receptors in angiogenesis," Cytokine Growth Factor Rev. 13(1):75-85.
Dong et al., 2002, "Some new aspects in biosensors," J. Biotechnol. 82(4):303-323.
Easty et al., 1997, "Loss of expression of receptor tyrosine kinase family genes PTK7 and SEK in metastatic melanoma," Int. J. Cancer 71(6):1061-1065.
Ellis et al., 1996, "A juxtamembrane autophosphorylation site in the Eph family receptor tyrosine kinase, Sek, mediates high affinity interaction with p59fyn," Oncogene 12(8):1727-1736.
Fisher et al., 1994, "Surface plasmon resonance based methods for measuring the kinetics and binding affinities of biomolecular interactions," Curr. Opin. Biotechnol. 5(4):389-395.
Fivash et al., 1998, "BIAcore for macromolecular interaction," Curr. Opin. Biotechnol. 9(1):97-101.
Fox et al., 1995, "cDNA cloning and tissue distribution of five human EPH-like receptor protein-tyrosine kinases," Oncogene 10(5):897-905.
Fry et al., 1995, "Inhibitors of protein tyrosine kinases," Curr. Opin. Biotechnol. 6(6):662-667.
Haseloff et al., 1988, "Simple RNA enzymes with new and highly specific endoribonuclease activities," Nature 334(6183):585-591.
Hunter, 1997, "Oncoprotein networks," Cell 88(3):333-346.
Kinch et al., 2003, "Overexpression and functional alterations of the EphA2 tyrosine kinase in cancer," Clin. Exp. Metastasis 20(1):59-68.
Kondapaka et al., 1996, "Tyrosine kinase inhibitor as a novel signal transduction and antiproliferative agent: prostate cancer," Mol. Cell. Endocrinol. 117(1):53-58.
Kuang et al., 1998, "Differential screening and suppression subtractive hybridization identified genes differentially expressed in an estrogen receptor-positive breast carcinoma cell line," Nucleic Acids Res. 26(4):1116-1123.
Levitzki et al., 1995, "Tyrosine kinase inhibition: an approach to drug development," Science 267(5205):1782-1788.
Logsdon et al., 2003, "Molecular profiling of pancreatic adenocarcinoma and chronic pancreatitis identifies multiple genes differentially regulated in pancreatic cancer," Cancer Res. 63(10):2649-2657.

(Continued)

*Primary Examiner*—Laura B Goddard

(57) ABSTRACT

The invention provides agonistic anti-EphA4 antibodies.

9 Claims, 8 Drawing Sheets

OTHER PUBLICATIONS

Figure 1:
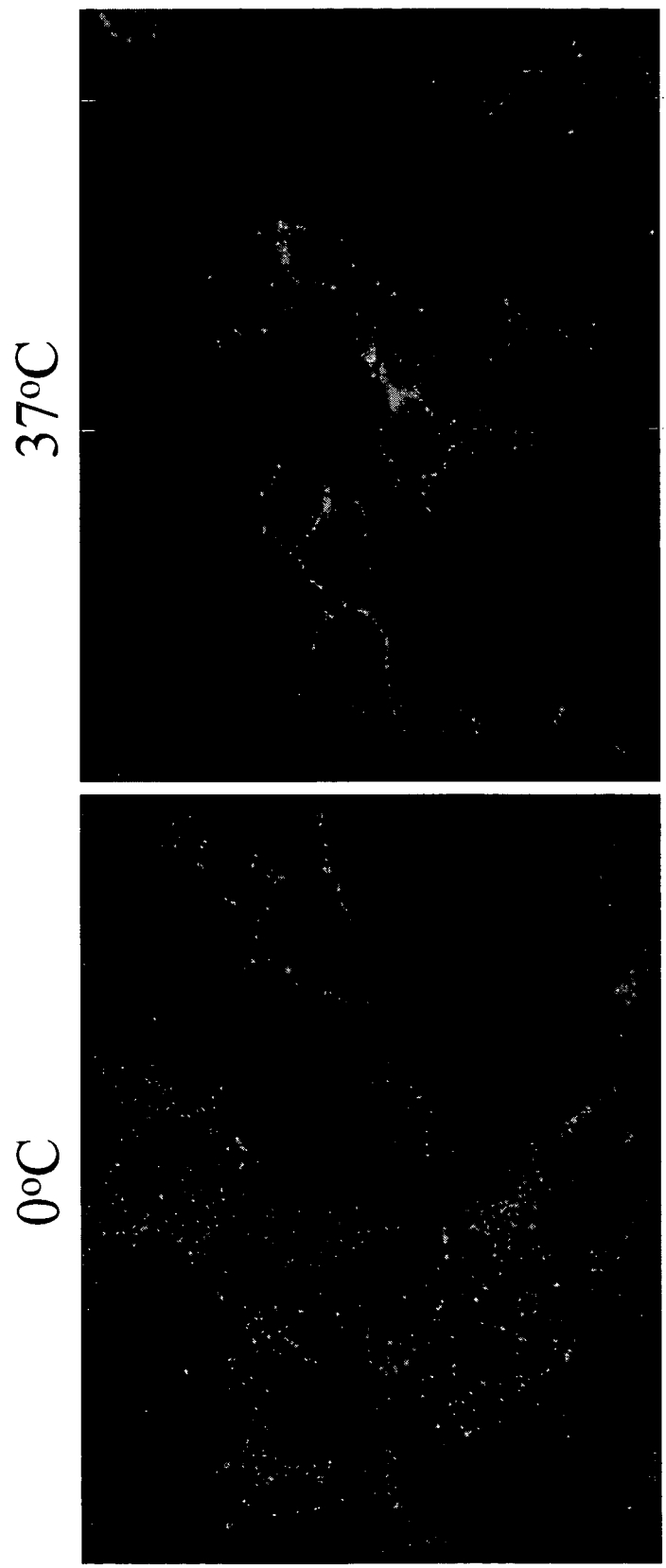

Malik et al., 1996, "Integrin-mediated signaling in normal and malignant cells: a role of protein tyrosine kinases," Biochim. Biophys. Acta 1287(2-3):73-76.

Martone et al., 1997, "Immunolocalization of the receptor tyrosine kinase EphA4 in the adult rat central nervous system," Brain Res. 771(2):238-250.

Meric et al., 2002, "Expression profile of tyrosine kinases in breast cancer," Clin. Cancer. Res. 8(2):361-367.

Miao et al., 2000, "Activation of EphA2 kinase suppresses integrin function and causes focal-adhesion-kinase dephosphorylation," Nat. Cell Biol. 2(2):62-69.

Morton et al., 1995, "Interpreting complex binding kinetics from optical biosensors: a comparison of analysis by linearization, the integrated rate equation, and numerical integration," Anal. Biochem. 227(1):176-185.

Mullett et al., 2000, "Surface plasmon resonance-based immunoassays," Methods 22(1):77-91.

Myszka, 1997, "Kinetic analysis of macromolecular interactions using surface plasmon resonance biosensors," Curr. Opin. Biotechnol. 8(1):50-57.

Nemoto et al., 1997, "Overexpression of protein tyrosine kinases in human esophageal cancer," Pathobiology 65(4):195-203.

O'Shannessy, 1994, "Determination of kinetic rate and equilibrium binding constants for macromolecular interactions: a critique of the surface plasmon resonance literature," Curr. Opin. Biotechnol. 5(1):65-71.

Parsons, 1996, "Integrin-mediated signalling: regulation by protein tyrosine kinases and small GTP-binding proteins," Curr. Opin. Cell Biol. 8(2):146-152.

Pasquale, 1997, "The Eph family receptors," Curr. Opin. Cell. Biol. 9(5):608-615.

Patarca, 1996, "Protein phosphorylation and dephosphorylation in physiologic and oncologic processes," Crit. Rev. Oncog. 7(5-6):343-432.

Rhim et al., 1997, "Human prostate carcinogenesis," Crit. Rev. Oncog. 8(4):305-328.

Rich et al., 2000, "Advances in surface plasmon resonance biosensor analysis," Curr. Opin. Biotechnol. 11(1):54-61.

Winning et al., 2002, "EphA4 catalytic activity causes inhibition of RhoA GTPase in Xenopus laevis embryos," Differentiation 70(1):46-55.

Zelinski et al., 2001, "EphA2 overexpression causes tumorigenesis of mammary epithelial cells," Cancer Res. 61(5):2301-2306.

\* cited by examiner

Crosslink w/:
LX13 ScFv, then anti Flag

Immunoprecipitate w/:
Ephrin A4-Fc

Blot w/:
anti phospho-tyrosine

Fig. 7A

```
ATGAAAAAATTATTATTCGCAATTCCTTTAGTTGTTCCTTTTCTATGCGGGCCATGGCCAGCCGGGCCATGGCCAGCTGTTGCAGTCTGGAGCTGAGGTGAAGAAGCCTGGGGCCTCAGTG
TACTTTTTTAATAATAAGCGTTAAGGAAATCAACAAGGAAAGATACGCGGCCCGGTCGGCCGGTACCGGTGTCCACGTGTCGACAACGTCAGACCTCGACTCCACTTCTTCGGACCCCGAGTCAC
Met Lys Lys Leu Leu Phe Ala Ile Pro Leu Val Pro Phe Tyr Ala Ala Gln Pro Ala Met Ala Gln Val Gln Leu Leu Gln Ser Gly Ala Glu Val Lys Lys Pro Gly Ala Ser Val
      protein III leader Seq.                                                                    EphA4-44-VH AAGGTTCCCTGCAAGGCTTCTGGATACACCTTCACTAGCTATGCTATGAGTGCAGCAGGCCCCTGGACAGGGCTTGAGTGGATGGGATCAACACCAACACTGGGAACCCA
TTCCAAGGGACGTTCCGAAGACCTATGTGGAAGTGATCGATACGATACTCAAACCACGCTGTCCCGGGACCTGTTCCCGAACTCACCTACCTACCTAGTTGTTGTTGTTGTGACCCTTGGGT
Lys Val Pro Cys Lys Ala Ser Gly Tyr Thr Phe Thr Ser Tyr Ala Met Ser Trp Val Arg Gln Ala Pro Gly Gln Gly Leu Glu Trp Met Gly Trp Ile Asn Thr Asn Thr Gly Asn Pro
                                          Ser Tyr Ala Met Ser              EphA4-44-VH                          Trp Ile Asn Thr Gly Asn Pro
                                              HCDR1                                                                    HCDR2

ACGTATGCCCAGGGACTTCACAGGACGGTTTGTCTTCCCTTGGACACACCTCTGTCAGCACGGCATATCTGCAGATCAGCAGCCTAAAGGCTGAGGACACTGCCGTGTATTACTGTGCGAGA
TGCATACGGGTCCCTGAAGTGTCCTGCCAAACAGAGAAGGGAACCCTGTGGAGACAGTCGTGCCGTATAGACGTCTAGTCGTCGGATTTCCGACTCGTCGGAGCACATAATGACACGCTCT
Thr Tyr Ala Gln Gly Phe Thr Gly Phe Val Phe Ser Leu Asp Thr Ser Val Ser Thr Ala Tyr Leu Gln Ile Ser Ser Leu Lys Ala Glu Asp Thr Ala Val Tyr Tyr Cys Ala Arg
                                                         EphA4-44-VH

GTCCGGACTACGGTGTGATGGGGACGGTATGGACGTCTGGGGCCAAGGGACCACCGTCACCGTCTCCTCAGGCGGCGGCGGATCCGAAATTGTGCTGACTCAGTCTCCAGCC
CAGGCCTGATGCCACACTACCCTGCCATACCTGCAGACCCCGGTTCCTGGTGGCAGTGGCAGAGAGTCCGCGGCCCGCACCGCCTAGCTGAGAGCGACTGAGTCAGAGGTCGG
Val Arg Thr Thr Val Tyr Gly Asp Gly Met Asp Val Trp Gly Gln Gly Thr Thr Val Thr Val Ser Ser Gly Gly Gly Gly Ser Gly Ile Val Leu Thr Gln Ser Pro Ala
Val Arg Thr Thr Val Tyr Gly Asp Gly Met Asp Val               EphA4-44-VH                        Linker              EphA4-44-VL
                    HCDR3

ACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTAT
TGGGACAGACAGAGAGGTCCCCCTTTCTCGGTGGAGAGGACGTCGTCAGTCTCACAATCGTCGTTGAATCGGACCGGTCGTCTTTGGACCGGTCCGAGGTCCGAGGAGTAGATA
Thr Leu Ser Val Ser Pro Gly Glu Arg Ala Thr Leu Ser Cys Arg Ala Ser Gln Ser Val Ser Ser Asn Leu Ala Trp Tyr Gln Gln Lys Pro Gly Gln Ala Pro Arg Leu Leu Ile Tyr
                                                            EphA4-44-VL
                                                  Arg Ala Ser Gln Ser Val Ser Ser Asn Leu Ala
                                                                LCDR1
```

EPHA4 ANTIBODIES

This application claims priority to U.S. Provisional Patent application No. 60/476,909, filed Jun. 6, 2003, and U.S. Provisional Patent application No. 60/503,356, filed Sep. 16, 2003, each of which is incorporated by reference herein in its entirety.

1. FIELD OF THE INVENTION

The present invention relates to methods and compositions designed for the treatment, management, or prevention of hyperproliferative cell disease, particularly cancer. The methods of the invention comprise the administration of an effective amount of one or more antibodies specific for EphA4, preferably monoclonal antibodies, that are EphA4 agonists, inhibit a cancer cell phenotype (such as colony formation in soft agar or tubular network formation in a three dimensional basement membrane or extracellular membrane preparation, such as MATRIGEL™), preferentially bind epitopes on EphA4 that are selectively exposed or increased on cancer cells but not non-cancer cells and/or bind EphA4 with a $K_{off}$ of less than $3 \times 10^{-3}$ $s^{-1}$. The invention also provides pharmaceutical compositions comprising one or more monoclonal antibodies of the invention either alone or in combination with one or more other agents useful for cancer therapy. Diagnostic methods and methods for screening for therapeutically useful EphA4 specific antibodies are also provided.

2. BACKGROUND OF THE INVENTION

Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and, if current trends continue, cancer is expected to be the leading cause of death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A cure for cancer has yet to be found. Current treatment options, such as surgery, chemotherapy and radiation treatment, are often either ineffective or present serious side effects.

Metastasis

The most life-threatening forms of cancer often arise when a population of tumor cells gains the ability to colonize distant and foreign sites in the body. These metastatic cells survive by overriding restrictions that normally constrain cell colonization into dissimilar tissues. For example, typical mammary epithelial cells will generally not grow or survive if transplanted to the lung, yet lung metastases are a major cause of breast cancer morbidity and mortality. Recent evidence suggests that dissemination of metastatic cells through the body can occur long before clinical presentation of the primary tumor. These micrometastatic cells may remain dormant for many months or years following the detection and removal of the primary tumor. Thus, a better understanding of the mechanisms that allow for the growth and survival of metastatic cells in a foreign microenvironment is critical for the improvement of therapeutics designed to fight metastatic cancer and diagnostics for the early detection and localization of metastases.

Cancer Cell Signaling

Cancer is a disease of aberrant signal transduction. Aberrant cell signaling overrides anchorage-dependent constraints on cell growth and survival (Rhim, et al., *Critical Reviews in Oncogenesis* 8:305, 1997; Patarca, *Critical Reviews in Oncogenesis* 7:343, 1996; Malik, et al., *Biochimica et Biophysica Acta* 1287:73, 1996; Cance, et al., *Breast Cancer Res Treat* 35:105, 1995). Tyrosine kinase activity is induced by ECM anchorage and indeed, the expression or function of tyrosine kinases is usually increased in malignant cells (Rhim, et al., *Critical Reviews in Oncogenesis* 8:305,1997; Cance, et al., *Breast Cancer Res Treat* 35:105, 1995; Hunter, *Cell* 88:333, 1997). Based on evidence that tyrosine kinase activity is necessary for malignant cell growth, tyrosine kinases have been targeted with new therapeutics (Levitzki, et al., *Science* 267:1782, 1995; Kondapaka, et al., *Molecular & Cellular Endocrinology* 117:53, 1996; Fry, et al., *Current Opinion in BioTechnology* 6: 662, 1995). Unfortunately, obstacles associated with specific targeting to tumor cells often limit the application of these drugs. In particular, tyrosine kinase activity is often vital for the function and survival of benign tissues (Levitzki, et al., *Science* 267:1782, 1995). To minimize collateral toxicity, it is critical to identify and then target tyrosine kinases that are selectively overexpressed in tumor cells.

EphA4

EphA4 is a receptor tyrosine kinase that is expressed in brain, heart, lung, muscle, kidney, placenta, pancreas (Fox, et al, *Oncogene* 10:897, 1995) and melanocytes (Easty, et al., *Int. J. Cancer* 71:1061, 1997). EphA4 binds cell membrane-anchored ligands (Ephrins A1, A2, A3, A4, A5, B2, and B3; Pasquale, *Curr. Opin. in Cell Biology,* 1997, 9:608; also ligands B61, AL1/RAGS, LERK4, Htk-L, and Elk-L3; Martone, et al., *Brain Research* 771:238, 1997), and ligand binding leads to EphA4 autophosphorylation on tyrosine residues (Ellis, et al., *Oncogene* 12:1727, 1996). EphA4 tyrosine phosphorylation creates a binding region for proteins with Src Homology 2/3 (SH2/SH3) domains, such as the cytoplasmic tyrosine kinase p59fyn (Ellis, et al., supra; Cheng, et al., *Cytokine and Growth Factor Reviews* 13:75, 2002). Activation of EphA4 in Xenopus embryos leads to loss of cadherin-dependent cell adhesion (Winning, et al., *Differentiation* 70:46, 2002; Cheng, et al., supra), suggesting a role for EphA4 in tumor angiogenesis; however, the-role of EphA4 in cancer progression is unclear. EphA4 appears to be upregulated in breast cancer, esophageal cancer, and pancreatic cancer (Kuang, et al., *Nucleic Acids Res.* 26:1116, 1998; Meric, et al, *Clinical Cancer Res.* 8:361, 2002; Nemoto, et al., *Pathobiology* 65:195, 1997; Logsdon, et al., *Cancer Res.* 63:2649, 2003), yet it is downregulated in melanoma tissue (Easty, et al., supra).

Cancer Therapy

One barrier to the development of anti-metastasis agents has been the assay systems that are used to design and evaluate these drugs. Most conventional cancer therapies target rapidly growing cells. However, cancer cells do not necessarily grow more rapidly but instead survive and grow under conditions that are non-permissive to normal cells (Lawrence and Steeg, 1996, *World J. Urol.* 14:124-130). These fundamental differences between the behaviors of normal and malignant cells provide opportunities for therapeutic targeting. The paradigm that micrometastatic tumors have already disseminated throughout the body emphasizes the need to evaluate potential chemotherapeutic drugs in the context of a foreign and three-dimensional microenvironment. Many standard cancer drug assays measure tumor cell growth or survival under typical cell culture conditions (i.e., monolayer growth). However, cell behavior in two-dimensional assays often does not reliably predict tumor cell behavior in vivo.

Currently, cancer therapy may involve surgery, chemotherapy, hormonal therapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). Recently, cancer therapy may also involve biological therapy or immunotherapy. All of these approaches can pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and, although it can be effective, is often used to prevent or delay recurrence of cancer after other treatments have removed the majority of the cancer cells. Biological therapies/immunotherapies are limited in number and each therapy is generally effective for a very specific type of cancer.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (see, for example, Gilman et al., Goodman and Gilman's: The Pharmacological Basis of Therapeutics, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. Further, it is uncommon for cancer to be treated by only one method. Thus, there is a need for development of new therapeutic agents for the treatment of cancer and new, more effective, therapy combinations for the treatment of cancer.

3. SUMMARY OF THE INVENTION

EphA4 is over expressed in a number of cancers. The inventors have found that EphA4 antibody binding to EphA4 can decrease proliferation and/or metastatic behavior of a cell, and causes phosphorylation of EphA4 and an EphA4-associated protein of approximately 75 kilodaltons (kDa). The present inventors believe that EphA4 may play a role in tumorigenesis and metastasis similar to that of EphA2. Antibodies that agonize EphA2, i.e., elicit EphA2 signaling, actually decrease EphA2 expression and inhibit tumor cell growth and/or metastasis, as described in co-pending U.S. patent application Ser. No. 10/436,782, entitled "EphA2 Monoclonal Antibodies and Methods of Use Thereof" filed May 12, 2003. The inventors have also discovered that antibody binding of EphA4 is sufficient to decrease cell-ECM attachments and induce cell rounding. Cell-ECM attachments are generally understood to provide physical attachments and intracellular signaling that govern many aspects of cell behavior, including decisions regarding cell growth, migration, invasion and differentiation. Thus, EphA4 antibody binding to EphA4 correlates with increased EphA4 phosphorylation and decreased cell-ECM attachment. Although not intending to be bound by any mechanism of action, antibodies or other molecules that agonize EphA4 may repress hyperproliferation or malignant cell behavior by inducing EphA4 autophosphorylation, thereby causing subsequent EphA4 degradation to down-regulate expression. Thus, in one embodiment, the EphA4 antibodies of the invention agonize EphA4 signaling and increase phosphorylation of EphA4 and the EphA4-associated 75 kDa protein ("EphA4 agonistic antibodies").

In addition, cancer cells exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation, such as MATRIGEL™. Non-cancer cells do not form colonies in soft agar and form distinct sphere-like structures in three-dimensional basement membrane or extracellular matrix preparations. The present inventors have also found that anti-EphA4 antibodies can reduce growth of EphA4-expressing cancer cells in soft agar. Accordingly, the invention also provides antibodies that specifically bind EphA4 and inhibit one or more cancer cell phenotypes, such as colony formation in soft agar or tubular network formation in three-dimensional basement membrane or extracellular matrix preparations ("cancer cell phenotype inhibitory EphA4 antibodies"). Exposing cancer cells to such cancer cell phenotype inhibitory EphA4 antibodies prevents or decreases the cells' ability to colonize or form tubular networks in these substrates. Furthermore, in certain embodiments, the addition of such cancer cell phenotype inhibitory EphA4 antibodies to already established colonies of cancer cells cause a reduction or elimination of an existing cancer cell colony, i.e., leads to killing of hyperproliferative and/or metastatic cells, for example through necrosis or apoptosis.

Differences in the subcellular localization, ligand binding properties or protein organization (e.g., structure, orientation in the cell membrane) may further distinguish the EphA4 that is present on cancer cells from EphA4 on non-cancer cells. In non-cancer cells, EphA4 is expressed at low levels. However, cancer cells generally display decreased cell-cell contacts and this may decrease EphA4-ligand binding. Furthermore, the overexpression of EphA4 may cause an excess of EphA4 relative to ligand that increases the amount of non-ligand bound EphA4. Consequently, changes in the subcellular distribution or membrane orientation of EphA4 may cause EphA4 to localize to sites in a cancer cell where it is inaccessible to ligand. Additionally, EphA4 may have altered ligand binding properties (e.g., due to an altered conformation) in cancer cells such that it is incapable of stable interactions with its ligand whether or not it is localized to the cell-cell junction. In each case, these changes can expose certain epitopes on the EphA4 in cancer cells that are not exposed in non-cancer cells. Accordingly, the invention also provides antibodies that specifically bind EphA4 but preferably bind an EphA4 epitope exposed on cancer cells but not on non-cancer cells ("exposed EphA4 epitope antibodies"). Exposing cancer cells to such EphA4 antibodies that preferentially bind epitopes on EphA4 that are selectively exposed or increased on cancer cells but not non-cancer cells targets the therapeutic/prophylactic antibody to cancer cells and prevents or decreases the cells' ability to proliferate while sparing non-cancer cells.

Antibodies that bind EphA4 with a very low $K_{off}$ rate may be particularly effective to reduce EphA4 expression and/or induce EphA4 degradation and, thereby, inhibit tumor cell growth and/or metastasis and/or proliferation of hyperproliferative cells. Accordingly, the invention further provides antibodies that bind EphA4 with a $K_{off}$ of less than $3\times10^{-3}$ $s^{-1}$ and, preferably, are EphA4 agonists.

The present invention provides for the screening and identification of antibodies that bind to EphA4 and agonize EphA4, inhibit a cancer cell phenotype, preferentially bind epitopes on EphA4 that are selectively exposed or increased on cancer cells but not non-cancer cells and/or have a $K_{off}$ less than $3\times10^{-3}$ $s^{-1}$, preferably monoclonal antibodies. In particular, the antibodies of the invention bind to the extracellular domain of EphA4 and, preferably, elicit EphA4 signaling and EphA4 autophosphorylation, inhibit a cancer cell phenotype, preferentially bind an EphA4 epitope exposed on cancer cells but not non-cancer cells, and/or have a $K_{off}$ of less than $3\times10^{-3}$ $s^{-1}$. The antibodies of the invention may further be used to modulate EphA4 signaling and phosphorylation of EphA4-associated proteins, such as a 75 kDa protein that is phosphorylated on tyrosine residues following crosslinking of EphA4 with EphA4 antibodies. Antibodies that modulate phosphorylation of this 75 kDa EphA4-associated protein can have value as therapeutic agents. In a specific embodiment, the invention provides the EphA4 scFv antibody EphA4-44/EA44 (in the specification herein, EA44 and EphA4-44 refer to the same antibody, that is, the EphA4-44 scFv clone which binds to EphA4 and was deposited with the ATCC on Jun. 10, 2004 as "EA44"). In a preferred embodiment, the invention provides an EphA4 antibody wherein the variable heavy chain and/or variable light chain amino acid sequence possesses at least 90% sequence identity with or is identical to the variable heavy chain or light chain amino acid sequence of EA44, as contained SEQ IDs NO: 4 and 8, respectively. In other preferred embodiments, the invention provides an EphA4 antibody wherein at least three, at least four, at least five, or all six of its CDRs are identical to the corresponding CDRs in EA44. In other specific embodiments, the invention provides anti-EphA4 scFv clones 8, 18, 20, 36, and 41.

In particular, the invention provides an antibody comprising (or alternatively, consisting of) the EA44 VH CDR1 (SEQ ID NO. 22) and VL CDR1 (SEQ ID NO. 28); the EA44 VH CDR1 (SEQ ID NO. 22) and VL CDR2 (SEQ ID NO. 30); the EA44 VH CDR1 (SEQ ID NO. 22) and VL CDR3 (SEQ ID NO. 32); the EA44 VH CDR2 (SEQ ID NO. 24) and VL CDR1 (SEQ ID NO. 28); the EA44 VH CDR2 (SEQ ID NO. 24) and VL CDR2 (SEQ ID NO. 30); the EA44 VH CDR2 (SEQ ID NO. 24) and VH CDR3 (SEQ ID NO. 26); the EA44 VH CDR3 (SEQ ID NO. 26) and VH CDR1 (SEQ ID NO. 22); the EA44 VH CDR3 (SEQ ID NO; 26) and VL CDR2 (SEQ ID NO. 30); the EA44 VH CDR3 (SEQ ID NO. 26) and VL CDR3 (SEQ ID NO. 32); the EA44 VH1 CDR1, VH CDR2 (SEQ ID NO. 24) and VL CDR1 (SEQ ID NO. 28); the EA44 VH CDR1 (SEQ ID NO. 22), VH CDR2 (SEQ ID NO. 24) and VL CDR2 (SEQ ID NO. 30); the EA44 VH CDR1 (SEQ ID NO. 22), VH CDR2 (SEQ ID NO. 24) and VL CDR3 (SEQ ID NO. 32); the EA44 VH CDR2 (SEQ ID NO. 24), VH CDR3 (SEQ ID NO. 26) and VL CDR1 (SEQ ID NO. 28), the EA44 VH CDR2 (SEQ ID NO. 24), VH CDR3 (SEQ ID NO. 26) and VL CDR2 (SEQ ID NO. 30); the EA44 VH CDR2 (SEQ ID NO. 24), VH CDR2 (SEQ ID NO. 24) and VL CDR3 (SEQ ID NO. 32); the EA44 VH CDR1 (SEQ ID NO. 22), VL CDR1 (SEQ ID NO. 28) and VL CDR2 (SEQ ID NO. 30); the EA44 VH CDR1 (SEQ ID NO. 22), VL CDR1 (SEQ ID NO. 28) and VL CDR3 (SEQ ID NO. 32); the EA44 VH CDR2 (SEQ ID NO. 24), VL CDR1 (SEQ ID NO. 28) and VL CDR2 (SEQ ID NO. 30); the EA44 VH CDR2 (SEQ ID NO. 24), VL CDR1 (SEQ ID NO. 28) and VL CDR3 (SEQ ID NO. 32); the EA44 VH CDR3 (SEQ ID NO. 26), VL CDR1 (SEQ ID NO. 28) and VL CDR2 (SEQ ID NO. 30); the EA44 VH CDR3 (SEQ ID NO. 26), VL CDR1 (SEQ ID NO. 28) and VL CDR3 (SEQ ID NO. 32); the EA44 VH CDR1 (SEQ ID NO. 22), VH CDR2 (SEQ ID NO. 24), VH CDR3 (SEQ ID NO. 26) and VL CDR1 (SEQ ID NO. 28); the EA44 VH CDR1 (SEQ ID NO. 22), VH CDR2 (SEQ ID NO. 24), VH CDR3 (SEQ ID NO. 26) and VL CDR2 (SEQ ID NO. 30); the EA44 VH CDR1 (SEQ ID NO. 22), VH CDR2 (SEQ ID NO. 24), VH CDR3 (SEQ ID NO. 26) and VL CDR3 (SEQ ID NO. 32); the EA44VH CDR1 (SEQ ID NO. 22), VH CDR2 (SEQ ID NO. 24), VL CDR1 (SEQ ID NO. 28) and VL CDR2 (SEQ ID NO. 30); the EA44 VH CDR1 (SEQ ID NO. 22), VH CDR2 (SEQ ID NO. 24), VL CDR1 (SEQ ID NO. 28) and VL CDR3 (SEQ ID NO. 32); the EA44 VH CDR1 (SEQ ID NO. 22), VH CDR3 (SEQ ID NO. 26), VL CDR1 (SEQ ID NO. 28) and VL CDR2 (SEQ ID NO. 30); the EA44 VH CDR1 (SEQ ID NO. 22), VH CDR3 (SEQ ID NO. 26), VL CDR1 (SEQ ID NO. 28) and VL CDR3 (SEQ ID NO. 32); the EA44 VH CDR2 (SEQ ID NO. 24), VH CDR3 (SEQ ID NO. 26), VL CDR1 (SEQ ID NO. 28) and VL CDR2 (SEQ ID NO. 30); the EA44 VH CDR2 (SEQ ID NO. 24), VH CDR3 (SEQ ID NO. 26), VL CDR1 (SEQ ID NO. 28) and VL CDR3 (SEQ ID NO. 32); the EA44 VH CDR2 (SEQ ID NO. 24), VH CDR3 (SEQ ID NO. 26), VL CDR2 (SEQ ID NO. 30) and VL CDR3 (SEQ ID NO. 32); the EA44 VH CDR1 (SEQ ID NO. 22), VH CDR2 (SEQ ID NO. 24), VH CDR3 (SEQ ID NO. 26), VL CDR1 (SEQ ID NO. 28) and VL CDR2 (SEQ ID NO. 30); the EA44 VH CDR1 (SEQ ID NO. 22), VH CDR2 (SEQ ID NO. 24), VH CDR3 (SEQ ID NO. 26), VL CDR1 (SEQ ID NO. 28) and VL CDR3 (SEQ ID NO. 32); the EA44 VH CDR1 (SEQ ID NO. 22), VH CDR2 (SEQ ID NO. 24), VL CDR1 (SEQ ID NO. 28), VL CDR2 (SEQ ID NO. 30), and VL CDR3 (SEQ ID NO. 32); the EA44 VH CDR1 (SEQ ID NO. 22), VH CDR3 (SEQ ID NO. 26), VL CDR1 (SEQ ID NO. 28), VL CDR2 (SEQ ID NO. 30), and VL CDR3 (SEQ ID NO. 32); the EA44 VH CDR2 (SEQ ID NO. 24), VH CDR3 (SEQ ID NO. 26), VL CDR1 (SEQ ID NO. 28), VL CDR2 (SEQ ID NO. 30), and VL CDR3 (SEQ ID NO. 32); or any combination thereof of the EA44 VH CDRs and VL CDRs listed in FIG. 7.

In another embodiment, an EphA4 agonistic antibody comprises a VH CDR encoded by a nucleic acid sequence having a nucleotide sequence of SEQ ID NO. 21, 23, or 25. In another embodiment, an EphA4 agonistic antibody comprises a VL CDR encoded by a nucleic acid sequence having a nucleotide sequence of SEQ ID NO. 27, 29, or 30. In another embodiment, an EphA4 agonistic antibody comprises a VH CDR and a VL CDR encoded by a nucleic acid sequence having a nucleotide sequence of SEQ ID NO. 21, 23, or 25, and SEQ ID NO. 27, 29, or 30, respectively.

Accordingly, the present invention relates to pharmaceutical compositions and prophylactic and therapeutic regimens designed to prevent, treat, or manage a disease associated with overexpression of EphA4, particularly cancer, particularly metastatic cancer, in a subject comprising administering one or more antibodies that specifically bind to and agonize EphA4, inhibit a cancer cell phenotype (such as colony formation in soft agar or tubular network formation in a three dimensional basement membrane or extracellular membrane preparation, such as MATRIGEL™), preferentially bind epitopes on EphA4 that are selectively exposed or increased on cancer cells but not non-cancer cells and/or have a $K_{off}$ less than $3 \times 10^{-3}$ $s^{-1}$. In preferred embodiments, the EphA4 antibody decreases the size of colonies already formed in soft agar and/or reduces the extent of tubular network formation in a three-dimensional basement membrane or extracellular matrix preparation. In one embodiment, the cancer is of an epithelial cell origin. In another embodiment, the cancer is a cancer of the skin, lung, colon, prostate, breast, or bladder, or is a renal cell carcinoma or a melanoma. In a preferred embodiment, the cancer is a cancer of the pancreas. In another preferred embodiment, the cancer cells in the cancer to be prevented, treated, or managed overexpress EphA4. In a preferred embodiment, some EphA4 is not bound to ligand, either as a result of decreased cell-cell contacts, altered subcellular localization, or increases in amount of EphA4 relative to ligand. In further preferred embodiments, the EphA4 agonist is an EphA4 antibody wherein the variable heavy and/or variable light sequence possesses at least 90% sequence identity with the variable heavy or light sequence of EA44, as contained SEQ IDs NO: 22, 24, 26, 28, 30, and 32 respectively. In other preferred embodiments, the invention provides an EphA4 antibody wherein at least three, at least four, at least five, or all six of its CDRs are identical to the corresponding CDRs in EA44. In other specific embodiments, the invention provides anti-EphA4 scFv clones 8, 18, 20, 36, and 41.

In a preferred embodiment, the methods of the invention are used to prevent, treat, or manage metastasis of tumors. The antibodies of the invention can be administered in combination with one or more other cancer therapies. In particular, the present invention provides methods of preventing, treating, or managing cancer in a subject comprising administering to said subject a therapeutically or prophylactically effective amount of one or more EphA4 antibodies of the invention in combination with the administration of a therapeutically or prophylactically effective amount of one or more chemotherapies, hormonal therapies, biological therapies/immunotherapies and/or radiation therapies other than the administration of an EphA4 antibody of the invention or in combination with surgery. In a preferred embodiment, one or more EphA4 antibodies are administered in combination with one or more EphA2 antibodies.

In other embodiments, the EphA4 antibodies of the invention are used to treat, prevent and/or manage a disease or disorder associated with cell hyperproliferation, such as but not limited to cancer, asthma, chronic obstructive pulmonary disease, inflammatory diseases of the bowel, intestine, stomach, and other vital organs, restenosis (smooth muscle and/or endothelial), Crohn's disease, psoriasis, and other non-metastatic diseases. In preferred embodiments, the hyperproliferative cells are epithelial. In preferred embodiments, the hyperproliferative cells overexpress EphA4. In a preferred embodiment, some EphA4 is not bound to ligand, either as a result of decreased cell-cell contacts, altered subcellular localization, or increases in amount of EphA4 relative to EphA4-ligand.

The methods and compositions of the invention are useful not only in untreated patients but are also useful in the treatment of patients partially or completely refractory to current standard and experimental cancer therapies, including but not limited to chemotherapies, hormonal therapies, biological therapies, radiation therapies, and/or surgery as well as to improve the efficacy of such treatments. Accordingly, in a preferred embodiment, the invention provides therapeutic and prophylactic agonists for the treatment or prevention of cancer that has been shown to be or may be refractory or non-responsive to therapies other than those comprising administration of EphA4 antibodies of the invention. In a specific embodiment, one or more EphA4 antibodies of the invention are administered to a patient refractory or non-responsive to a non-EphA4-based treatment, particularly tamoxifen treatment or a treatment in which resistance is associated with increased IL-6 levels, to render the patient non-refractory or responsive. The treatment to which the patient had previously been refractory or non-responsive can then be administered with therapeutic effect.

In addition, the present invention provides methods of screening for EphA4 antibodies of the invention. In particular, antibodies may be screened for binding to EphA4, particularly the extracellular domain of EphA4, using routine immunological techniques. In one embodiment, to identify agonistic EphA4 antibodies, EphA4 antibodies may be screened for the ability to elicit EphA4 signaling, e.g., increase EphA4 phosphorylation and/or phosphorylation of a 75 kDa EphA4-associated protein and/or to degrade EphA4.

In another embodiment, to identify cancer cell phenotype inhibiting antibodies, anti-EphA4 antibodies may be screened for the ability to prevent or reduce cancer cell colony formation in soft agar or reduce or inhibit tubular network formation in a three-dimensional basement membrane or extracellular matrix preparation, or any other method that detects a decrease in a cancer phenotype, for example, any assay that detects an increase in contact inhibition of cell proliferation (e.g., reduction of colony formation in a monolayer cell culture). In preferred embodiments, the antibodies are screened for ability to decrease the size of existing colonies in soft agar or reduce the extent or tubular matrix formation in the three-dimensional basement membrane or extracellular matrix preparation, particular induces cell (particularly cancer cell, more particularly metastatic cancer cell, but also including other hyperproliferative cell) necrosis or apoptosis. Additionally, antibodies may be screened for their ability to inhibit or reduce colony formation in soft agar and/or tubular network formation in three-dimensional basement membrane or extracellular matrix preparations in the presence of other anti-cancer agents, e.g., hormonal, chemotherapeutic, biologic or other anti-cancer agents.

In another embodiment, to identify antibodies that preferentially bind an EphA4 epitope exposed on cancer cells but not non-cancer cells, antibodies may be screened for the ability to preferentially bind EphA4 that is not bound to ligand, e.g., Ephrin A4, and that is not localized to cell-cell contacts. Any method known in the art to determine antibody binding/localization on a cell can be used to screen candidate antibodies for desirable binding properties. In a specific embodiment, immunofluorescence microscopy or flow cytometry is used to determine the binding characteristics of an antibody. In this embodiment, antibodies that bind poorly to EphA4 when it is bound to ligand and localized to cell-cell contacts but bind well to free EphA4 on a cell are encompassed by the invention. In another specific embodiment, EphA4 antibodies are selected for their ability to compete with ligands (e.g., cell-anchored or purified ligands) for binding to EphA4 using cell-based or ELISA assays.

In another embodiment, antibodies are screened using antibody binding kinetic assays well known in the art (e.g. surface plasmon resonance based assays, such as a BIACORE™ assay) to identify antibodies having a $K_{off}$ rate less than $3\times10^{-3}$ s$^{-1}$.

In other embodiments, the invention provides methods of treating, preventing, or managing cancer, by administering therapeutic agents, other than EphA4 antibodies of the invention, that reduce EphA4 protein levels, for example but not by way of limitation, anti-sense nucleic acids specific for EphA4, double stranded EphA4 RNA that mediates RNA interference of EphA4 expression, anti-EphA4 ribozymes, etc., as well as other inhibitors of EphA4, for example, small molecule inhibitors of EphA4.

The invention further provides diagnostic methods using the EphA4 antibodies of the invention to evaluate the efficacy of cancer treatment, either EphA4-based or not EphA4-based. In general, increased EphA4 expression may be associated with increasingly invasive and metastatic cancers. Accordingly, a reduction in EphA4 expression with a particular treatment indicates that the treatment is reducing the invasiveness and/or metastatic potential of cancer. The diagnostic methods of the invention may also be used to prognose or predict the course of cancer or the outcomes of cancer therapy. In particular embodiments, the diagnostic methods of the invention provide methods of imaging and localizing metastases and methods of diagnosis and prognosis using tissues and fluids distal to the primary tumor site (as well as methods using tissues and fluids of the primary tumor), for example, whole blood, sputum, urine, serum, fine needle aspirates (i.e., biopsies). In other embodiments, the diagnostic methods of the invention provide methods of imaging and localizing metastases and methods of diagnosis and prognosis in vivo. In such embodiments, primary metastatic tumors are detected using an antibody of the invention, preferably an exposed EphA4 epitope antibody. The antibodies of the invention may also be used for immunohistochemical analyses of frozen or fixed cells or tissue assays. In addition, the antibodies and diagnostic methods of the invention may be used to diagnose, prognose or monitor therapy of (whether EphA4 or non-EphA4-based therapy) non-cancer hyperproliferative diseases (particularly associated with EphA4 overexpression), for example, but not limited to, asthma, psoriasis, inflammatory bowel disease, restenosis, Crohn's disease, prostatic intraepithelial neoplasia (PIN), chronic obstructive pulmonary disease, etc.

In another embodiment, kits comprising the pharmaceutical compositions or diagnostic reagents of the invention are provided.

3.1 Definitions

As used herein, the term "agonist" refers to any compound including a protein, polypeptide, peptide, antibody, antibody fragment, large molecule, or small molecule (less than 10 kD), that increases the activity, activation or function of another molecule. EphA4 agonists cause increased phosphorylation of EphA4 and/or the 75 kDa EphA4-associated protein, and degradation of EphA4 protein. EphA4 antibodies that agonize EphA4 may or may not also inhibit cancer cell phenotype (e.g., colony formation in soft agar or tubular network formation in a three-dimensional basement membrane or extracellular matrix preparation) and may or may not preferentially bind an EphA4 epitope that is exposed in a cancer cell relative to a non-cancer cell and may or may not have a low $K_{off}$ rate.

The term "antibodies or fragments thereof that immunospecifically bind to EphA4" as used herein refers to antibodies or fragments thereof that specifically bind to an EphA4 polypeptide or a fragment of an EphA4 polypeptide and do not specifically bind to other polypeptides. Preferably, antibodies or fragments that immunospecifically bind to an EphA4 polypeptide or fragment thereof do not non-specifically cross-react with other antigens (e.g., binding cannot be competed away with a non-EphA4 protein, e.g., BSA). Antibodies or fragments that immunospecifically bind to an EphA4 polypeptide can be identified, for example, by immunoassays or other techniques known to those of skill in the art. Antibodies of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. In particular, antibodies of the present invention include immunoglobulin molecules and immunologically active portions of immunoglobulin molecules, i.e., molecules that contain an antigen binding site that immunospecifically binds to an EphA4 antigen (e.g., one or more complementarity determining regions (CDRs) of an anti-EphA4 antibody). Preferably agonistic antibodies or fragments that immunospecifically bind to an EphA4 polypeptide or fragment thereof preferentially agonize EphA4 and do not significantly agonize other activities.

As used herein, the term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation, such as MATRIGEL™. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells.

As used herein, the phrase "cancer cell phenotype inhibiting" refers to the ability of a compound to prevent or reduce cancer cell colony formation in soft agar or tubular network formation in a three-dimensional basement membrane or extracellular matrix preparation or any other method that detects a reduction in a cancer cell phenotype, for example, assays that detect an increase in contact inhibition of cell proliferation (e.g., reduction of colony formation in a monolayer cell culture). Cancer cell phenotype inhibiting compounds may also cause a reduction or elimination of colonies when added to established colonies of cancer cells in soft agar or the extent of tubular network formation in a three-dimensional basement membrane or extracellular matrix preparation. EphA4 antibodies that inhibit cancer cell phenotype may or may not also agonize EphA4 and may or may not have a low $K_{off}$ rate.

The term "derivative" as used herein refers to a polypeptide that comprises an amino acid sequence of an EphA4 polypeptide, a fragment of an EphA4 polypeptide, an antibody that immunospecifically binds to an EphA4 polypeptide, or an antibody fragment that immunospecifically binds to an EphA4 polypeptide, that has been altered by the introduction of amino acid residue substitutions, deletions or additions. The term "derivative" as used herein also refers to an EphA4 polypeptide, a fragment of an EphA4 polypeptide, an antibody that immunospecifically binds to an EphA4 polypeptide, or an antibody fragment that immunospecifically binds to an EphA4 polypeptide which has been modified, i.e, by the covalent attachment of any type of molecule to the polypeptide. For example, but not by way of limitation, an EphA4 polypeptide, a fragment of an EphA4 polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of an EphA4 polypeptide, a fragment of an EphA4 polypeptide, an antibody, or antibody fragment may be modified by chemical modifications using techniques known to those of skill in the art, including, but not limited to, specific chemical cleavage, acetylation, formylation, metabolic synthesis of tunicamycin, etc. Further, a derivative of an EphA4 polypeptide, a fragment of an EphA4 polypeptide, an antibody, or antibody fragment may contain one or more non-classical amino acids. In one embodiment, a polypeptide derivative possesses a similar or identical function as an EphA4 polypeptide, a fragment of an EphA4 polypeptide, an antibody, or antibody fragment described herein. In another embodiment, a derivative of EphA4 polypeptide, a fragment of an EphA4 polypeptide, an antibody, or antibody fragment has an altered activity when compared to an unaltered polypeptide. For example, a derivative antibody or fragment thereof can bind to its epitope more tightly or be more resistant to proteolysis.

The term "epitope" as used herein refers to a portion of an EphA4 polypeptide having antigenic or immunogenic activity in an animal, preferably in a mammal, and most preferably in a mouse or a human. An epitope having immunogenic activity is a portion of an EphA4 polypeptide that elicits an antibody response in an animal. An epitope having antigenic activity is a portion of an EphA4 polypeptide to which an antibody immunospecifically binds as determined by any method well known in the art, for example, by immunoassays. Antigenic epitopes need not necessarily be immunogenic.

The "fragments" described herein include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of an EphA4 polypeptide or an antibody that immunospecifically binds to an EphA4 polypeptide. Preferably, antibody fragments are epitope-binding fragments.

As used herein, the term "humanized antibody" refers to forms of non-human (e.g., murine) antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al. 1994, *PNAS* 91:969-973; Tan et al., 2002, *J. Immunol.* 169:1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596.

As used herein, the term "hyperproliferative cell disorder" refers to a disorder that is not neo-plastic in which cellular hyperproliferation causes or contributes to the pathological state or symptoms of the disorder. In some embodiments, the hyperproliferative cell disorder is characterized by hyperproliferating epithelial cells. Hyperproliferative epithelial cell disorders include, but are not limited to, asthma, COPD, lung fibrosis, bronchial hyper responsiveness, psoriasis, seborrheic dermatitis, and cystic fibrosis. In other embodiments, the hyperproliferative cell disorder is characterized by hyperproliferating endothelial cells. Hyperproliferative endothelial cell disorders include, but are not limited to restenosis, hyperproliferative vascular disease, Behcet's Syndrome, atherosclerosis, and macular degeneration.

As used herein, the term "hypervariable region" refers to the amino acid residues of an antibody which are responsible for antigen binding. The hypervariable region comprises amino acid residues from a "Complementarity Determining Region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined.

As used herein, the term "in combination" refers to the use of more than one prophylactic and/or therapeutic agents. The use of the term "in combination" does not restrict the order in which prophylactic and/or therapeutic agents are administered to a subject with a hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a hyperproliferative cell disorder, especially cancer. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

As used herein, the phrase "low tolerance" refers to a state in which the patient suffers from side effects from treatment so that the patient does not benefit from and/or will not continue therapy because of the adverse effects and/or the harm from the side effects outweighs the benefit of the treatment.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the term "neoplastic" refers to a disease involving cells that have the potential to metastasize to distal sites and exhibit phenotypic traits that differ from those of non-neoplastic cells, for example, formation of colonies in a three-dimensional substrate such as soft agar or the formation of tubular networks or weblike matrices in a three-dimensional basement membrane or extracellular matrix preparation, such as MATRIGEL™. Non-neoplastic cells do not form colonies in soft agar and form distinct sphere-like structures in three-dimensional basement membrane or extracellular matrix preparations. Neoplastic cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. Thus, "non-neoplastic" means that the condition, disease, or disorder does not involve cancer cells.

As used herein, the phrase "non-responsive/refractory" is used to describe patients treated with one or more currently available therapies (e.g., cancer therapies) such as chemotherapy, radiation therapy, surgery, hormonal therapy and/or biological therapy/immunotherapy, particularly a standard therapeutic regimen for the particular cancer, wherein the therapy is not clinically adequate to treat the patients such that these patients need additional effective therapy, e.g., remain unsusceptible to therapy. The phrase can also describe patients who respond to therapy yet suffer from side effects, relapse, develop resistance, etc. In various embodiments, "non-responsive/refractory" means that at least some significant portion of the cancer cells are not killed or their cell division arrested. The determination of whether the cancer cells are "non-responsive/refractory" can be made either in vivo or in vitro by any method known in the art for assaying the effectiveness of treatment on cancer cells, using the art-accepted meanings of "refractory" in such a context.

In various embodiments, a cancer is "non-responsive/refractory" where the number of cancer cells has not been significantly reduced, or has increased during the treatment.

As used herein, the term "potentiate" refers to an improvement in the efficacy of a therapeutic agent at its common or approved dose.

As used herein, the terms "prevent," "preventing" and "prevention" refer to the prevention of the onset, recurrence, or spread of a disease in a subject resulting from the administration of a prophylactic or therapeutic agent.

As used herein, the term "prophylactic agent" refers to any agent that can be used in the prevention of the onset, recurrence or spread of a disease or disorder associated with EphA4 overexpression and/or cell hyperproliferative disease, particularly cancer. In certain embodiments, the term "prophylactic agent" refers to an EphA4 agonistic antibody, an EphA4 cancer cell phenotype inhibiting antibody, an exposed EphA4 epitope antibody, or an antibody that binds EphA4 with a low $K_{off}$. In certain other embodiments, the term "prophylactic agent" refers to cancer chemotherapeutics, radiation therapy, hormonal therapy, biological therapy (e.g., immunotherapy), and/or EphA4 antibodies of the invention. In other embodiments, more than one prophylactic agent may be administered in combination.

As used herein, a "prophylactically effective amount" refers to that amount of the prophylactic agent sufficient to result in the prevention of the onset, recurrence or spread of cell hyperproliferative disease, preferably, cancer. A prophylactically effective amount may refer to the amount of prophylactic agent sufficient to prevent the onset, recurrence or spread of hyperproliferative disease, particularly cancer, including but not limited to those predisposed to hyperproliferative disease, for example, those genetically predisposed to cancer or previously exposed to carcinogens. A prophylactically effective amount may also refer to the amount of the prophylactic agent that provides a prophylactic benefit in the prevention of hyperproliferative disease. Further, a prophylactically effective amount with respect to a prophylactic agent of the invention means that amount of prophylactic agent alone, or in combination with other agents, that provides a prophylactic benefit in the prevention of hyperproliferative disease. Used in connection with an amount of an EphA4 antibody of the invention, the term can encompass an amount that improves overall prophylaxis or enhances the prophylactic efficacy of or synergies with another prophylactic agent.

As used herein, a "protocol" includes dosing schedules and dosing regimens.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* (56$^{th}$ ed., 2002).

As used herein, the terms "single-chain Fv" and "scFv" refer to antibody fragments comprising the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds. Springer-Verlag, N.Y., pp. 269-315 (1994). In specific embodiments, scFvs include bi-specific scFvs and humanized scFvs.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "treat," "treating" and "treatment" refer to the eradication, reduction or amelioration of symptoms of a disease or disorder, particularly, the eradication, removal, modification, or control of primary, regional, or metastatic cancer tissue that results from the administration of one or more therapeutic agents. In certain embodiments, such terms refer to the minimizing or delaying the spread of cancer resulting from the administration of one or more therapeutic agents to a subject with such a disease.

As used herein, the term "therapeutic agent" refers to any agent that can be used in the prevention, treatment, or management of a disease or disorder associated with overexpression of EphA4 and/or cell hyperproliferative diseases or disorders, particularly, cancer. In certain embodiments, the term "therapeutic agent" refers to an EphA4 agonistic antibody, an EphA4 cancer cell phenotype inhibiting antibody, an exposed EphA4 epitope antibody, or an antibody that binds EphA4 with a $K_{off}$ of less than $3\times10^{-3}$ s$^{-1}$, a non-antibody agent that agonizes EphA4, such as an EphA4 ligand or EphA4-binding fragment or derivative thereof, or an agent that reduces EphA4 expression, such as EphA4 RNAi, antisense, etc. In certain other embodiments, the term "therapeutic agent" refers to cancer chemotherapeutics, radiation therapy, hormonal therapy, biological therapy/immunotherapy, and/or EphA4 antibody of the invention. In other embodiments, more than one therapeutic agent may be administered in combination.

As used herein, a "therapeutically effective amount" refers to that amount of the therapeutic agent sufficient to treat or manage a disease or disorder associated with EphA4 overexpression and/or cell hyperproliferative disease and, preferably, the amount sufficient to destroy, modify, control or remove primary, regional or metastatic cancer tissue. A therapeutically effective amount may refer to the amount of therapeutic agent sufficient to delay or minimize the onset of the hyperproliferative disease, e.g., delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of hyperproliferative disease or cancer. Used in connection with an amount of an EphA4 antibody of the invention, the term can encompass an amount that improves overall therapy, reduces or avoids unwanted effects, or enhances the therapeutic efficacy of or synergies with another therapeutic agent.

4. DESCRIPTION OF THE FIGURES

FIG. 1: EphA4 antibodies induce cell rounding. Aspc1 cells incubated with single chain Fv antibodies (scFv) that bind EphA4 show cell rounding when incubated at 37° C. relative to cells incubated at 0° C.

Figure 2:
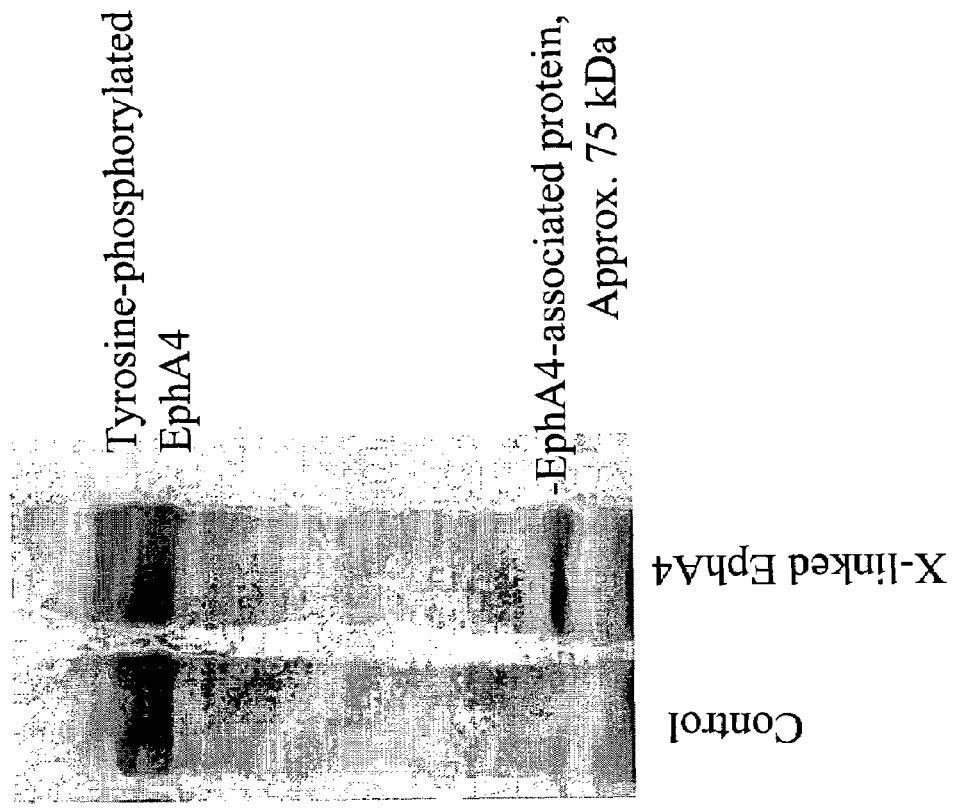

FIG. 2: Crosslinking of EphA4 causes tyrosine phosphorylation of an associated 75 kDa protein. Cells were incubated with LX13 scFv, then crosslinked by anti-Flag antibody, immunoprecipitated with Ephrin A4-Fc, and blotted with anti-phosphotyrosine. Cross-linked EphA4 ("X-linked EphA4") shows increased tyrosine phosphorylation of an EphA4-associated 75 kDa protein, relative to control cells ("Control") that are not cross-linked.

Figure 3:
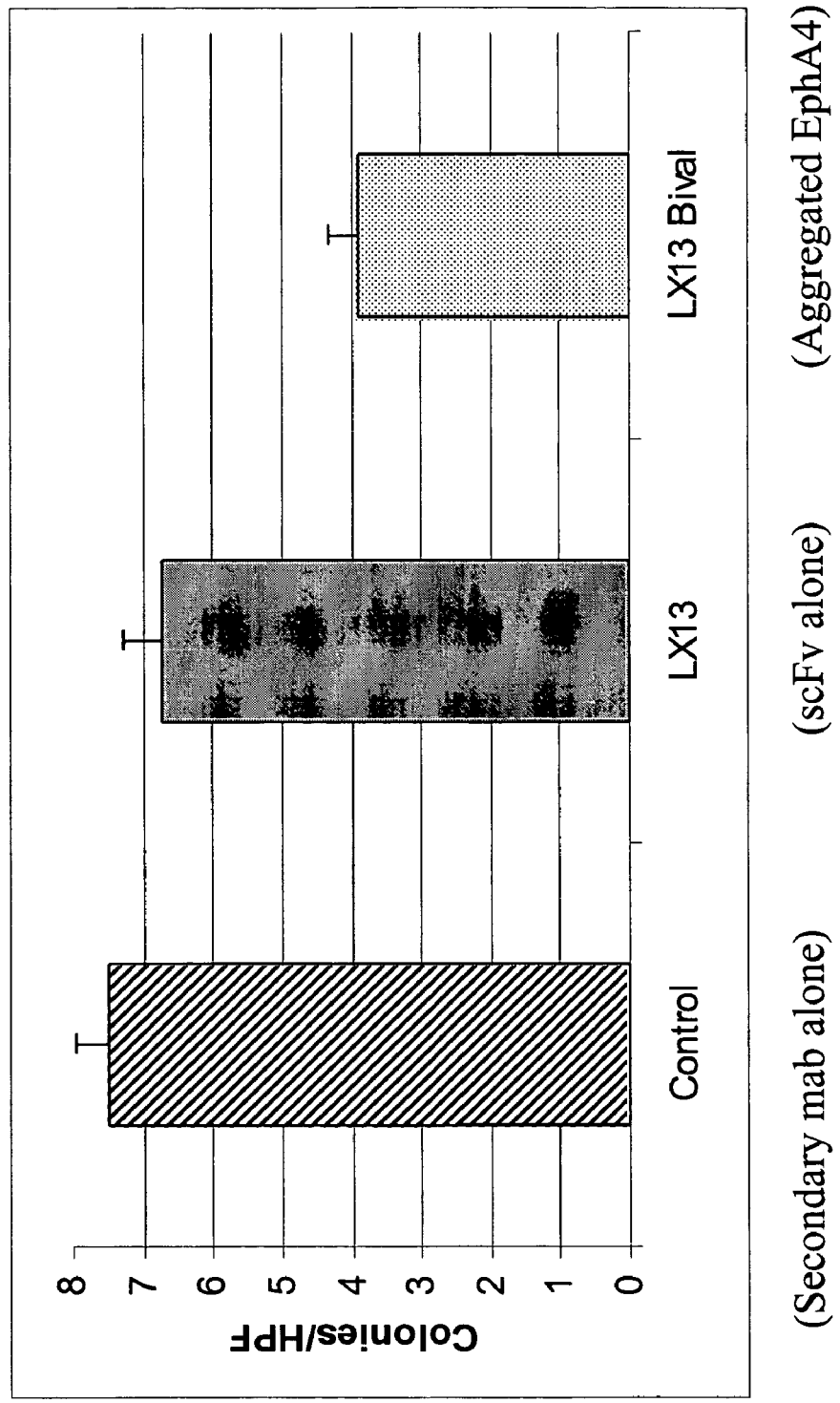

FIG. 3: EphA4 aggregation inhibits soft agar growth of ASPC1 cells. Cells treated with EphA4 antibodies (scFv), which are then cross-linked with a secondary monoclonal antibody (mab; "LX13 Bival"), show significant decrease in colony formation in soft agar relative to cells treated with scFv alone ("LX13") or secondary mab alone ("Control").

Figure 4:
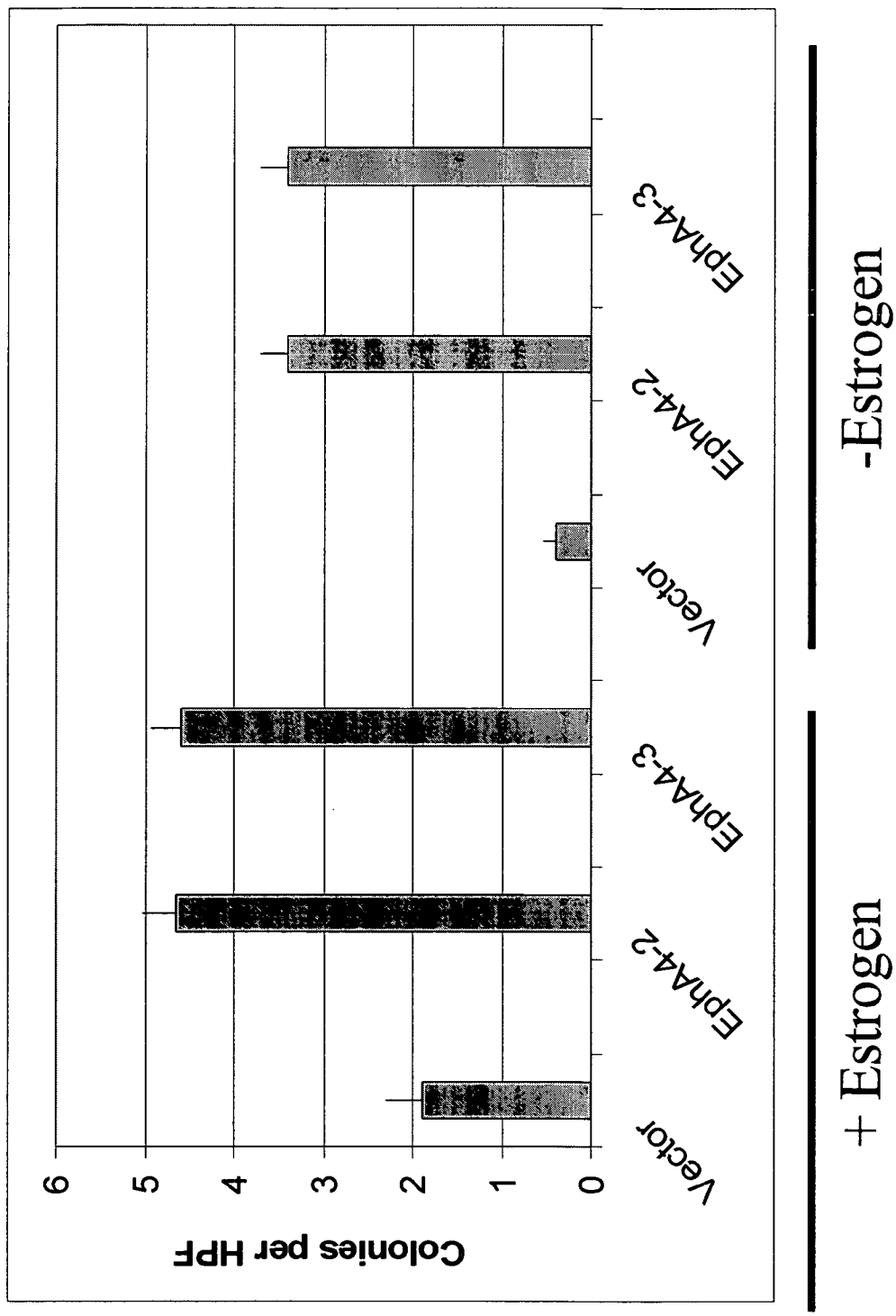

FIG. 4: EphA4 upregulation causes a decreased dependence on estrogen for cell growth in a mammary carcinoma cell line. MCF-7 cells, which normally express very low levels of EphA4, were transfected with empty vector ("Vector") or vector containing EphA4 sequence. Stable expressors of EphA4 were isolated (clones 2 and 3,"EphA4-2" and "EphA4-3"). In soft agar assays in which the cells were incubated with estrogen, MCF-7-EphA4 cells demonstrated a 2.4 fold increase in anchorage independent growth compared to a vector-transfected control ("+Estrogen"). However in the absence of estrogen ("−Estrogen"), EphA4-expressing cells had an 8.5 fold increase in growth compared to vector-transfected controls.

Figure 5:

FIG. 5: EphA4 RNA levels are increased in pancreatic tumor tissue. Bar A: EphA4 RNA in pathologically normal pancreatic tissue from 52-year old male. Bar B: EphA4 RNA in pancreatic tissue displaying Stage 4A ductal pancreatic adenocarcinoma from same 52-year old male as in Bar A. Bar C: EphA4 RNA in pancreatic tissue displaying Stage 2A ductal pancreatic adenocarcinoma from 72-year old male. Bar D: EphA4 RNA in lymph node tissue of 71-year old female displaying Stage 2B metastatic pancreatic adenocarcinoma. Bar E: EphA4 RNA in omentum tissue of 57-year old female displaying Stage 4 metastatic pancreatic adenocarcinoma. Bar F: EphA4 RNA in liver tissue of 45-year old female displaying metastatic pancreatic adenocarcinoma.

Figure 6:
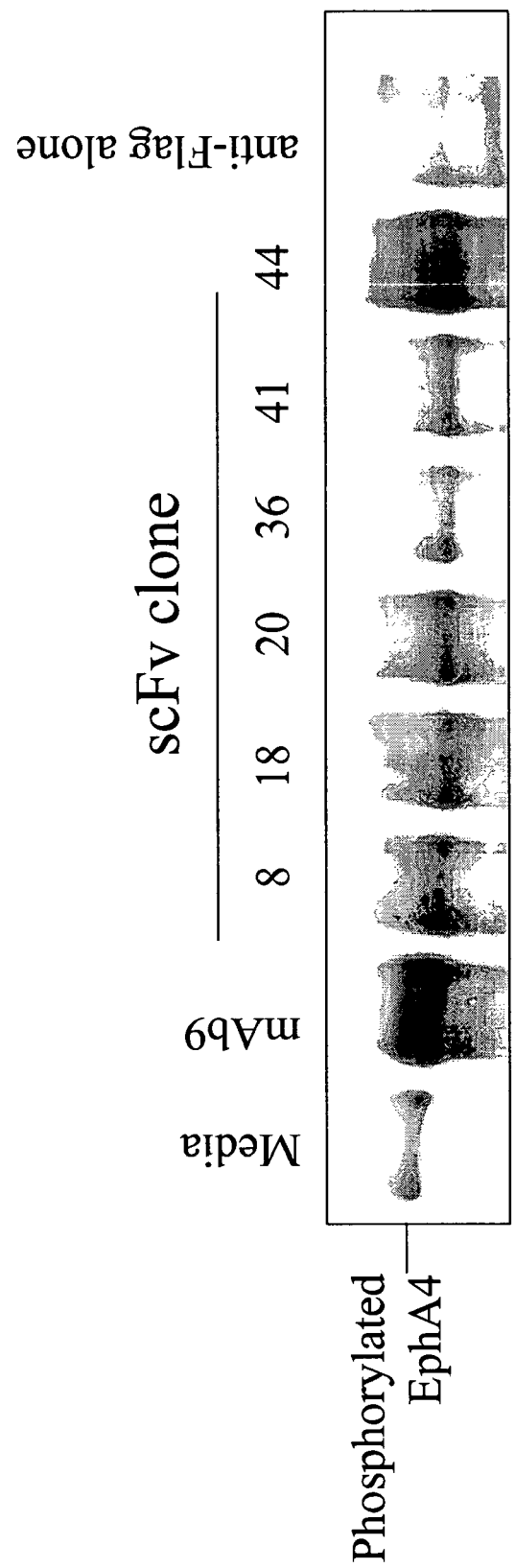

FIG. 6: Anti-EphA4 scFv clone 44 strongly induces tyrosine phosphorylation of EphA4. Anti-EphA4 scFv clones 8, 18, and 20 also weakly induce EphA4 tyrosine phosphorylation, relative to control cells in media or cells incubated with anti-Flag antibodies alone, which show low levels of EphA4 phosphorylation.

Figure 7B:
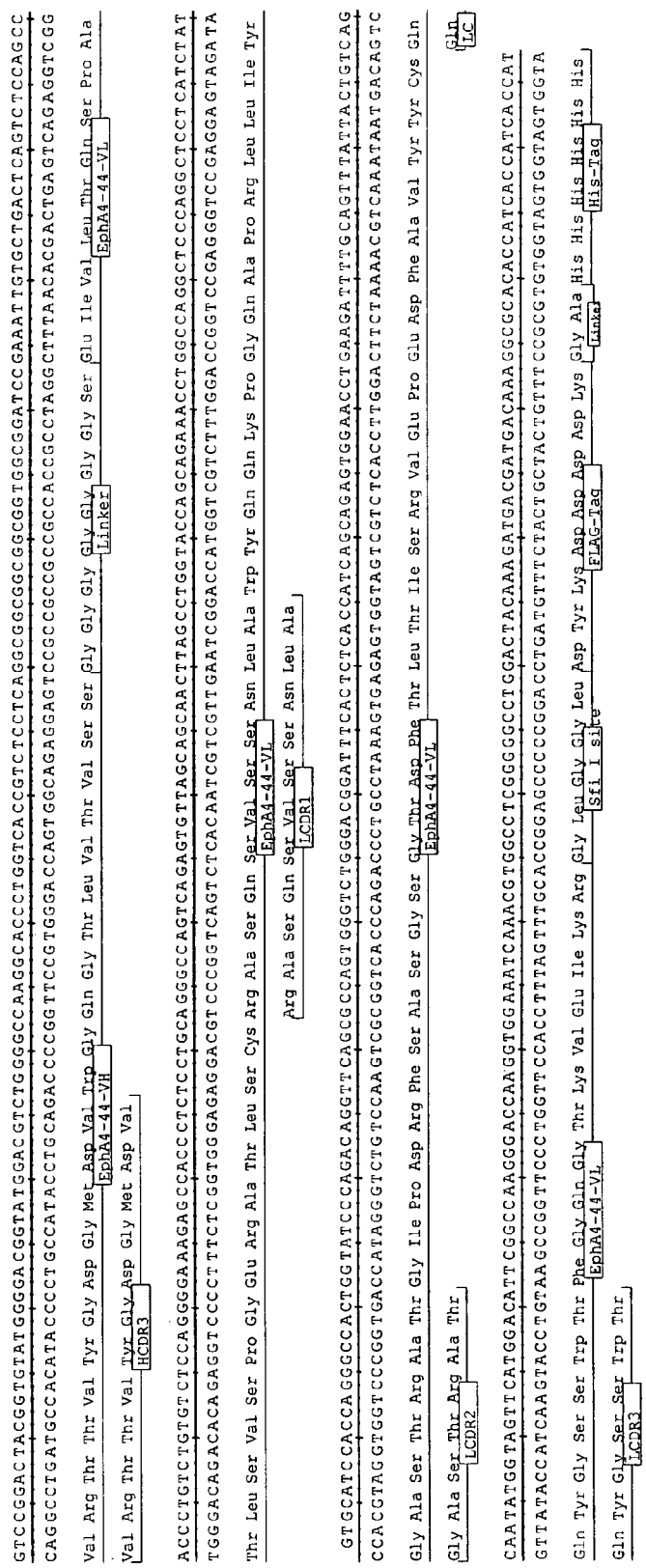

FIG. 7A, 7B: Sequence of scFV clone EphA4-44 (SEQ ID NO:17, 18). CDRs (HCDR1 SEQ ID NO:21,22; HCDR2 SEQ ID NO:23,24; HCDR3 SEQ ID NO: 25,26; LCDR1 SEQ ID NO:27,28; LCDR2 SEQ ID NO:29,30; LCDR3 SEQ ID NO:31,32), VH (SEQ ID NO:3,4), VL (SEQ ID NO:7,8), Protein III leader (SEQ ID NO: 1,2), Linker between VH and VL domains (SEQ ID NO: 5,6), Sfi I site (SEQ ID NO: 9,10), FLAG tag (SEQ ID NO: 11,12), and His tag (SEQ ID NO: 13,14) regions are indicated.

5. DETAILED DESCRIPTION OF THE INVENTION

The present invention is based, in part, on the inventors' discovery that EphA4 is upregulated in certain cancer cells and anti-EphA4 antibodies reduce certain cancer cell behaviors, such as cell attachment and growth in soft agar. Anti-EphA4 antibodies promote phosphorylation of EphA4 and an EphA4-associated protein. The present inventors also believe that EphA4 plays a role in cancer and cell proliferation similar to EphA2. EphA2 monoclonal antibodies that agonize EphA2 can inhibit cancer cell proliferation and invasiveness by reducing the levels of EphA2 expression in these cancer cells (see co-pending U.S. patent application Ser. No. 10/436,782, entitled "EphA2 Monoclonal Antibodies and Methods of Use Thereof" filed May 12, 2003). Decreased EphA4 activity or other results of EphA4 signaling may selectively inhibit malignant cancer cell growth. In particular, decreased levels of EphA4 and phosphorylation of EphA4 and/or a 75 kDa EphA4-associated protein may be achieved with EphA4 agonistic monoclonal antibodies. Although not intending to be bound by any mechanism of action, this inhibition of cell growth and/or metastasis may be achieved by stimulating (i.e., agonizing) EphA4 signaling thereby causing EphA4 phosphorylation which leads to the degradation of EphA4. Cancer cell growth may be decreased due to the decreased EphA4 levels and, therefore, decreased ligand-independent EphA4 signaling. Decreased EphA4 activity may also be achieved with EphA4 cancer cell phenotype inhibiting antibodies or antibodies that preferentially bind an EphA4 epitope exposed on cancer cells but not non-cancer cells. Additionally, antibodies that bind EphA4 with a low $K_{off}$ (e.g., less than $3\times10^{-3}$ $s^{-1}$) may also decrease EphA4 levels.

In addition, the inventors have found that antibody binding to EphA4 is sufficient to trigger changes in cell behavior. Specifically, EphA4 antibody binding to cells expressing EphA4 decreases cell-ECM attachments and induces cell rounding. Cell-ECM attachments are generally understood to provide physical attachments and intracellular signaling that govern many aspects of cell behavior, including decisions regarding cell growth, migration, invasion and differentiation. Consistent with this understanding, changes in cell interaction with its microenvironment have been linked with the initiation or progression of many different disease states. For example, increased ECM attachment can promote migration and proliferation and thereby trigger hyperproliferative diseases, which include but are not limited to: cancer; inflammatory diseases of the bowel (IBD), intestine (Crohn's disease), stomach and other vital organs; asthma; COPD and other hyperproliferative diseases of the lung; and restenosis, which is a clinical manifestation resulting from increased growth and migration of smooth muscle or endothelial cells. Therefore, EphA4 antibodies can be useful in the treatment of non-cancerous conditions in general, and for treatment of conditions linked with cell-ECM attachments in particular.

Accordingly, the present invention relates to methods and compositions that provide for the treatment, inhibition, and management of diseases and disorders associated with overexpression of EphA4 and/or cell hyperproliferative diseases and disorders. A particular aspect of the invention relates to methods and compositions containing compounds that inhibit cancer cell proliferation and invasion, particularly those cancer cells that overexpress EphA4. The present invention further relates to methods and compositions for the treatment, inhibition, or management of metastases of cancers of epithelial cell origin, especially human cancers of the breast, lung, skin, prostate, bladder, and pancreas, and renal cell carcinomas and melanomas. Further compositions and methods of the invention include other types of active ingredients in combination with the EphA4 antibodies of the invention. In other embodiments, the methods of the invention are used to treat, prevent or manage other diseases or disorders associated with cell hyperproliferation, for example but not limited to asthma, psoriasis, restenosis, COPD, etc.

The present invention also relates to methods for the treatment, inhibition, and management of cancer or other hyperproliferative cell disorder or disease that has become partially or completely refractory to current or standard cancer treatment, such as chemotherapy, radiation therapy, hormonal therapy, and biological therapy.

The invention further provides diagnostic methods using the EphA4 antibodies of the invention, particularly the exposed EphA4 epitope antibodies, to evaluate the efficacy of cancer treatment, either EphA4-based or not EphA4-based. The diagnostic methods of the invention can also be used to prognose or predict cancer progression. In particular embodiments, the diagnostic methods of the invention provide methods of imaging and localizing metastases and methods of diagnosis and prognosis using tissues and fluids distal to the primary tumor site (as well as methods using tissues and fluids of the primary tumor). In other embodiments, the diagnostic methods of the invention provide methods of imaging and localizing metastases and methods of diagnosis and prognosis in vivo.

In an additional embodiment, the invention provides methods of screening for anti-cancer agents, particularly antimetastatic cancer agents, by screening agents for the ability to decrease cell colonization in soft agar and/or tubular network formation in three-dimensional basement membrane and extracellular matrix preparations, such as MATRIGEL™. In preferred embodiments, the invention provides methods of screening for agents for the treatment and prevention of hyperproliferative diseases and disorders by assaying for the ability to reduce the extent of existing cell colonization in soft agar and/or tubular network formation in three-dimensional basement membrane. The present inventors found that inhibition of cell colonization in soft agar and/or tubular network formation in MATRIGEL™ is a far better indication of anti-metastatic activity and may identify potential anti-metastatic agents that would not have been identified by standard cell culture assays.

5.1 Antibodies

As discussed above, the invention encompasses administration of antibodies (preferably monoclonal antibodies) or fragments thereof that immunospecifically bind to and agonize EphA4 signaling ("EphA4 agonistic antibodies"); inhibit a cancer cell phenotype, e.g., inhibit colony formation in soft agar or tubular network formation in a three-dimensional basement membrane or extracellular matrix preparation, such as MATRIGEL™ ("cancer cell phenotype inhibiting antibodies"); preferentially bind epitopes on EphA4 that are selectively exposed or increased on cancer cells but not non-cancer cells ("exposed EphA4 epitope antibodies"); and/or bind EphA4 with a $K_{off}$ of less than $3\times10^{-3}$ $s^{-1}$. In one embodiment, the antibody binds to the extracellular domain of EphA4 and, preferably, also agonizes EphA4, e.g., increases EphA4 phosphorylation and/or phosphorylation of the 75 kDa EphA4-associated protein and, preferably, causes EphA4 degradation. In another embodiment, the antibody binds to the extracellular domain of EphA4 and, preferably, also inhibits and, even more preferably, reduces the extent of (e.g., by cell killing mechanisms such as necrosis and apoptosis) colony formation in soft agar or tubular network formation in a three-dimensional basement membrane or extracellular matrix preparation. In other embodiments, the antibodies inhibit or reduce a cancer cell phenotype in the presence of another anti-cancer agent, such as a hormonal, biologic, chemotherapeutic or other agent. In another embodiment, the antibody binds to the extracellular domain of EphA4 at an epitope that is exposed in a cancer cell but occluded in a non-cancer cell. In another embodiment, the antibody binds to the extracellular domain of EphA4, preferably with a $K_{off}$ of less than $1\times10^{-3}$ $s^{-1}$, more preferably less than $3\times10^{-3}$ $s^{-1}$. In other embodiments, the antibody binds to EphA4 with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$.

In a more preferred embodiment, the antibody binds to an EphA4 epitope and/or competes for EphA4 binding as assayed by ELISA or any other appropriate immunoassay. Cells that express the anti-EphA4 scFv EA44 have been deposited with the American Type Culture Collection (P.O. Box 1549, Manassas, Va. 20108) on Jun. 1, 2004 under the provisions of the Budapest Treaty on the International Recognition of the Deposit of Microorganisms for the Purposes of Patent Procedures, and assigned accession number PTA-6044 and is hereby incorporated by reference. In a specific embodiment, the invention provides the EphA4 scFv antibody EphA4-44/EA44 (in the specification herein, EA44 and EphA4-44 refer to the same antibody, that is, the EphA4-44 scFv clone which binds to EphA4 and was deposited with the ATCC on Jun. 10, 2004 as "EA44"). In a preferred embodiment, the invention provides an EphA4 antibody wherein the variable heavy chain and/or variable light chain amino acid sequence possesses at least 90% sequence identity with the variable heavy chain or light chain amino acid sequence of EA44, as contained SEQ IDs NO: 4 and 8, respectively. In other preferred embodiments, the invention provides an EphA4 antibody wherein at least three, at least four, at least five, or all six of its CDRs are identical to the corresponding CDRs in EA44. In other specific embodiments, the invention provides anti-EphA4 scFv clones 8, 18, 20, 36, and 41. In a most preferred embodiment, the antibody is human or has been humanized.

In other embodiments, the EphA4 antibody comprises the EA44 VH CDR 1 (SEQ ID NO. 22) and VL CDR1 (SEQ ID NO. 28); the EA44 VH CDR1 (SEQ ID NO. 22) and VL CDR2 (SEQ ID NO. 30); the EA44 VH CDR1 (SEQ ID NO. 22) and VL CDR3 (SEQ ID NO. 32); the EA44 VH CDR2 (SEQ ID NO. 24) and VL CDR1 (SEQ ID NO. 28); the EA44 VH CDR2 (SEQ ID NO. 24) and VL CDR2 (SEQ ID NO. 30); the EA44 VH CDR2 (SEQ ID NO. 24) and VH CDR3 (SEQ ID NO. 26); the EA44 VH CDR3 (SEQ ID NO. 26) and VH CDR1 (SEQ ID NO. 22); the EA44 VH CDR3 (SEQ ID NO. 26) and VL CDR2 (SEQ ID NO. 30); the EA44 VH CDR3 (SEQ ID NO. 26) and VL CDR3 (SEQ ID NO. 32); the EA44 VH1 CDR1, VH CDR2 (SEQ ID NO. 24) and VL CDR1 (SEQ ID NO. 28); the EA44 VH CDR1 (SEQ ID NO. 22), VH CDR2 (SEQ ID NO. 24) and VL CDR2 (SEQ ID NO. 30); the EA44 VH CDR1 (SEQ ID NO. 22), VH CDR2 (SEQ ID NO. 24) and VL CDR3 (SEQ ID NO. 32); the EA44 VH CDR2 (SEQ ID NO. 24), VH CDR3 (SEQ ID NO. 26) and VL CDR1 (SEQ ID NO. 28), the EA44 VH CDR2 (SEQ ID NO. 24), VH CDR3 (SEQ ID NO. 26) and VL CDR2 (SEQ ID NO. 30); the EA44 VH CDR2 (SEQ ID NO. 24), VH CDR2 (SEQ ID NO. 24) and VL CDR3 (SEQ ID NO. 32); the EA44 VH CDR1 (SEQ ID NO. 22), VL CDR1 (SEQ ID NO. 28) and VL CDR2 (SEQ ID NO. 30); the EA44 VH CDR1 (SEQ ID NO. 22), VL CDR1 (SEQ ID NO. 28) and VL CDR3 (SEQ ID NO. 32); the EA44 VH CDR2 (SEQ ID NO. 24), VL CDR1 (SEQ ID NO. 28) and VL CDR2 (SEQ ID NO.30); the EA44 VH CDR2 (SEQ ID NO. 24), VL CDR1 (SEQ ID NO. 28) and VL CDR3 (SEQ ID NO. 32); the EA44 VH CDR3 (SEQ ID NO. 26), VL CDR1 (SEQ ID NO. 28) and VL CDR2 (SEQ ID NO. 30); the EA44 VH CDR3 (SEQ ID NO. 26), VL CDR1 (SEQ ID NO. 28) and VL CDR3 (SEQ ID NO.32); the EA44 VH CDR1 (SEQ ID NO. 22), VH CDR2 (SEQ ID NO. 24), VH CDR3 (SEQ ID NO. 26) and VL CDR1 (SEQ ID NO. 28); the EA44 VH CDR1 (SEQ ID NO. 22), VH CDR2 (SEQ ID NO. 24), VH CDR3 (SEQ ID NO. 26) and VL CDR2 (SEQ ID NO. 30); the EA44 VH CDR1 (SEQ ID NO. 22), VH CDR2 (SEQ ID NO. 24), VH CDR3 (SEQ ID NO. 26) and VL CDR3 (SEQ ID NO. 32); the EA44VH CDR1 (SEQ ID NO. 22), VH CDR2 (SEQ ID NO. 24), VL CDR1 (SEQ ID NO. 28) and VL CDR2 (SEQ ID NO. 30); the EA44 VH CDR1 (SEQ ID NO. 22), VH CDR2 (SEQ ID NO. 24), VL CDR1 (SEQ ID NO. 28) and VL CDR3 (SEQ ID NO. 32); the EA44 VH CDR1 (SEQ ID NO. 22), VH CDR3 (SEQ ID NO. 26), VL CDR1 (SEQ ID NO. 28) and VL CDR2 (SEQ ID NO. 30); the EA44 VH CDR1 (SEQ ID NO. 22), VH CDR3 (SEQ ID NO. 26), VL CDR1 (SEQ ID NO. 28) and VL CDR3 (SEQ ID NO. 32); the EA44 VH CDR2 (SEQ ID NO. 24), VH CDR3 (SEQ ID NO. 26), VL CDR1 (SEQ ID NO. 28) and VL CDR2 (SEQ ID NO.30); the EA44 VH CDR2 (SEQ ID NO. 24), VH CDR3 (SEQ ID NO. 26), VL CDR1 (SEQ ID NO. 28) and VL CDR3 (SEQ ID NO. 32); the EA44 VH CDR2 (SEQ ID NO. 24), VH CDR3 (SEQ ID NO. 26), VL CDR2 (SEQ ID NO. 30) and VL CDR3 (SEQ ID NO. 32); the EA44 VH CDR1 (SEQ ID NO. 22), VH CDR2 (SEQ ID NO. 24), VH CDR3 (SEQ ID NO. 26), VL CDR1 (SEQ ID NO. 28) and VL CDR2 (SEQ ID NO. 30); the EA44 VH CDR1 (SEQ ID NO. 22), VH CDR2 (SEQ ID NO.

24), VH CDR3 (SEQ ID NO. 26), VL CDR1 (SEQ ID NO. 28) and VL CDR3 (SEQ ID NO. 32); the EA44 VH CDR1 (SEQ ID NO. 22), VH CDR2 (SEQ ID NO. 24), VL CDR1 (SEQ ID NO. 28), VL CDR2 (SEQ ID NO. 30), and VL CDR3 (SEQ ID NO. 32); the EA44 VH CDR1 (SEQ ID NO. 22), VH CDR3 (SEQ ID NO. 26), VL CDR1 (SEQ ID NO. 28), VL CDR2 (SEQ ID NO.30), and VL CDR3 (SEQ ID NO. 32); the EA44 VH CDR2 (SEQ ID NO. 24), VH CDR3 (SEQ ID NO. 26), VL CDR1 (SEQ ID NO. 28), VL CDR2 (SEQ ID NO. 30), and VL CDR3 (SEQ ID NO. 32); or any combination thereof of the EA44 VH CDRs and VL CDRs listed in FIG. 7.

Antibodies of the invention include, but are not limited to, monoclonal antibodies, synthetic antibodies, recombinantly produced antibodies, intrabodies, multispecific antibodies (including bi-specific antibodies), human antibodies, humanized antibodies, chimeric antibodies, single-chain Fvs (scFv) (including bi-specific scFvs) such as scFv clones 8, 18, 20, 36, 41, and EA44, Fab fragments, F(ab') fragments, disulfide-linked Fvs (sdFv), and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to EphA4 and is an agonist of EphA4, inhibits or reduces a cancer cell phenotype, preferentially binds an EphA4 epitope exposed on cancer cells but not non-cancer cells, and/or binds EphA4 with a $K_{off}$ of less than $3 \times 10^{-3}$ s$^{-1}$. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule.

The antibodies used in the methods of the invention may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice or other animals that express antibodies from human genes.

The antibodies used in the methods of the present invention may be monospecific, bispecific, trispecific or of greater multispecificity. Multispecific antibodies may immunospecifically bind to different epitopes of an EphA4 polypeptide or may immunospecifically bind to both an EphA4 polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547-1553.

In a preferred embodiment, antibodies of the invention are bispecific T cell engagers (BiTEs). Bispecific T cell engagers (BiTE) are bispecific antibodies that can redirect T cells for antigen-specific elimination of targets. A BiTE molecule has an antigen-binding domain that binds to a T cell antigen (e.g. CD3) at one end of the molecule and an antigen binding domain that will bind to an antigen on the target cell. A BiTE molecule was recently described in WO 99/54440, which is herein incorporated by reference. This publication describes a novel single-chain multifunctional polypeptide that comprises binding sites for the CD19 and CD3 antigens (CD19× CD3). This molecule was derived from two antibodies, one that binds to CD19 on the B cell and an antibody that binds to CD3 on the T cells. The variable regions of these different antibodies are linked by a polypeptide sequence, thus creating a single molecule. Also described, is the linking of the variable heavy chain (VH) and light chain (VL) of a specific binding domain with a flexible linker to create a single chain, bispecific antibody.

In an embodiment of this invention, an antibody or ligand that immunospecifically binds to EphA4 will comprise a portion of the BiTE molecule. For example, the VH and/or VL (preferably a scFV) of an antibody that binds EphA4 can be fused to an anti-CD3 binding portion such as that of the molecule described above, thus creating a BiTE molecule that targets EphA4. In addition to the variable heavy and or light chain of antibody against EphA4, other molecules that bind EphA4 can comprise the BiTE molecule, for example Ephrins A1, A2, A3, A4, A5, B2, and B3; B61, AL1/RAGS, LERK4, Htk-L, and Elk-L3. In another embodiment, the BiTE molecule can comprise a molecule that binds to other T cell antigens (other than CD3). For example, ligands and/or antibodies that immunospecifically bind to T-cell antigens like CD2, CD4, CD8, CD11a, TCR, and CD28 are contemplated to be part of this invention. This list is not meant to be exhaustive but only to illustrate that other molecules that can immunospecifically bind to a T cell antigen can be used as part of a BiTE molecule. These molecules can include the VH and/or VL portions of the antibody or natural ligands (for example LFA3 whose natural ligand is CD3). In one embodiment of the invention, the BiTE molecule is an EphA4 agonist. In another embodiment, the BiTE molecule is an EphA4 antagonist.

The "binding domain" as used in accordance with the present invention denotes a domain comprising a three-dimensional structure capable of specifically binding to an epitope like native antibodies, free scFv fragments or one of their corresponding immunoglobulin chains, preferably the VH chain. Thus, said domain can comprise the VH and/or VL domain of an antibody or an immunoglobulin chain, preferably at least the VH domain or more preferably the VH and VL domain linked by a flexible polypeptide linker (scFv). On the other hand, said binding domain contained in the polypeptide of the invention may comprise at least one complementarity determining region (CDR) of an antibody or immunoglobulin chain recognizing an antigen on the T cell or a cellular antigen. In this respect, it is noted that the binding domain present in the polypeptide of the invention may not only be derived from antibodies but also from other T cell or cellular antigen binding protein, such as naturally occurring surface receptors or ligands. It is further contemplated that in an embodiment of the invention, said first and or second domain of the above-described polypeptide mimic or correspond to a VH and VL region from a natural antibody. The antibody providing the binding site for the polypeptide of the invention can be, e.g., a monoclonal antibody, polyclonal antibody, chimeric antibody, humanized antibody, bispecific antibody, synthetic antibody, antibody fragment, such as Fab, Fv or scFv fragments etc., or a chemically modified derivative of any of these.

The antibodies used in the methods of the invention include derivatives that are modified, i.e., by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The present invention encompasses single domain antibodies, including camelized single domain antibodies (see e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079; which are incorporated herein by reference in their entireties). In one embodiment, the present invention provides single domain antibodies comprising two VH domains having the amino acid sequence of any of the VH domains of an EphA4 agonistic antibody, EphA4 cancer cell phenotype inhibiting antibody, exposed EphA4 epitope antibody, or an EphA4 antibody that binds EphA4 with a $K_{off}$ of less than $3 \times 10^{-3}$ s$^{-1}$ with modifications such that single domain antibodies are formed. In another embodiment, the present invention also provides single domain antibodies comprising two VH domains comprising one or more of the VH CDRs of an EphA4 agonistic antibody, EphA4 cancer cell phenotype inhibiting antibody, exposed EphA4 epitope antibody, or an EphA4 antibody that binds EphA4 with a $K_{off}$ of less than $3 \times 10^{-3}$ s$^{-1}$.

The methods of the present invention also encompass the use of antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

The present invention further encompasses antibodies or fragments thereof that immunospecifically bind to EphA4 and agonize EphA4 and/or inhibit a cancer cell phenotype, preferentially bind an EphA4 epitope exposed in cancer cells, and/or bind EphA4 with a $K_{off}$ of less than $3 \times 10^{-3}$ s$^{-1}$, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of an EphA4 antibody. The determination of percent identity of two amino acid sequences can be determined by any method known to one skilled in the art, including BLAST protein searches.

In a specific embodiment, the present invention encompasses antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of scFv clone EA44. In a further embodiment, the invention encompasses a recombinant EphA4 antibody or antibody fragment that is an EphA4 agonistic antibody, an EphA4 cancer cell phenotype inhibiting antibody, or an exposed EphA4 epitope antibody wherein the antibody comprises at least one of the complementarity determining regions (CDRs) of the variable light chain or variable heavy chain of the EA44 antibody wherein the amino acid sequences of the variable heavy and light chain sequences of EA44.

In another specific embodiment, the invention encompasses an EphA4 antibody or antibody fragment that is an EphA4 agonistic antibody, an EphA4 cancer cell phenotype inhibiting antibody, or an exposed EphA4 epitope antibody wherein said antibody comprises one, two, three, four, five, or all six of the complementarity determining regions (CDRs) of the variable light chain and/or variable heavy chain of the EA44 antibody.

5.1.1 Antibody Conjugates

The present invention encompasses the use of antibodies or fragments thereof (or other therapeutics, such as EphA4 ligands and EphA4-binding fragments thereof) recombinantly fused or chemically conjugated (including both covalent and non-covalent conjugations) to a heterologous agent. The heterologous agent may be a polypeptide (or portion thereof, preferably to a polypeptide of at least 10, at least 20, at least 30, at least 40, at least 50, at least 60, at least 70, at least 80, at least 90 or at least 100 amino acids), nucleic acid, small molecule (less than 1000 daltons), or inorganic or organic compound. The fusion does not necessarily need to be direct, but may occur through linker sequences. Antibodies fused or conjugated to heterologous agents may be used in vivo to detect, treat, manage, or monitor the progression of a disorder using methods known in the art. See e.g., International Publication WO 93/21232; EP 439,095; Naramura et al., 1994, *Immunol. Lett.* 39:91-99; U.S. Pat. No. 5,474,981; Gillies et al., 1992, *PNAS* 89:1428-1432; and Fell et al., 1991, *J. Immunol.* 146:2446-2452, which are incorporated by reference in their entireties. In some embodiments, the disorder to be detected, treated, managed, or monitored is malignant cancer that overexpresses EphA4. In other embodiments, the disorder to be detected, treated, managed, or monitored is pre-malignant cancer that overexpresses EphA4. In a specific embodiments, the pre-malignant cancer is high-grade prostatic intraepithelial neoplasia (PIN), ductal carcinoma of the breast, or compound nevi.

The present invention further includes compositions comprising heterologous agents fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622, 929, 5,359,046, 5,349,053, 5,447,851, and 5,112,946; EP 307,434; EP 367,166; International Publication Nos. WO 96/04388 and WO 91/06570; Ashkenazi et al., 1991, *PNAS* 88: 10535-10539; Zheng et al., 1995, *J. Immunol.* 154:5590-5600; and Vil et al., 1992, *PNAS* 89:11337- 11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions immunospecifically bind to EphA4 may be recombined with one or more components, motifs, sections, parts, domains, fragments, etc. of one or more heterologous agents.

In one embodiment, antibodies of the present invention or fragments or variants thereof are conjugated to a marker sequence, such as a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *PNAS* 86:821, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, *Cell* 37:767) and the "Flag" tag.

In other embodiments, antibodies of the present invention or fragments or variants thereof are conjugated to a diagnostic or detectable agent. Such antibodies can be useful for monitoring or prognosing the development or progression of a cancer as part of a clinical testing procedure, such as determining the efficacy of a particular therapy. Additionally, such antibodies can be useful for monitoring or prognosing the development or progression of a pre-malignant cancer (e.g., high-grade prostatic intraepithelial neoplasia (PIN), ductal carcinoma of the breast, or compound nevi). In one embodiment, an exposed EphA4 epitope antibody is conjugated to a diagnostic or detectable agent.

Such diagnosis and detection can accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^3$H), xenon ($^{133}$Xe), ytterbium ($^{169}$Yb, $^{179}$Yb), yttrium ($^{90}$Y), zinc ($^{65}$Zn); positron emitting metals using various positron emission tomographies, and nonradioactive paramagnetic metal ions.

In other embodiments, antibodies of the present invention or fragments or variants thereof are conjugated to a therapeutic agent such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In other embodiments, antibodies of the present invention or fragments or variants thereof are conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, *J. Immunol.*, 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

In other embodiments, antibodies of the present invention or fragments or variants thereof are conjugated to a therapeutic agent such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

In a specific embodiment, the conjugated antibody is an EphA4 antibody that preferably binds an EphA4 epitope exposed on cancer cells but not on non-cancer cells (i.e., exposed EphA4 epitope antibody). In another specific embodiment, the conjugated antibody is not EA2. In a further embodiment, the conjugated antibody comprises the variable light chain or variable heavy chain of the EA44 antibody.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, *Immunol. Rev.* 62:119-58. Methods for fusing or conjugating antibodies to polypeptide moieties are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al., 1991, *PNAS* 88: 10535-10539; Zheng et al., 1995, *J. Immunol.* 154:5590-5600; and Vil et al., 1992, *PNAS* 89:11337-11341. The fusion of an antibody to a moiety does not necessarily need to be direct, but may occur through linker sequences. Such linker molecules are commonly known in the art and described in Denardo et al., 1998, *Clin Cancer Res.* 4:2483-90; Peterson et al., 1999, *Bioconjug. Chem.* 10:553; Zimmerman et al., 1999, *Nucl. Med. Biol.* 26:943-50; Garnett, 2002, *Adv. Drug Deliv. Rev.* 53:171-216, each of which is incorporated herein by reference in its entirety.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.1.2 Methods of Producing Antibodies

The antibodies or fragments thereof can be produced by any method known in the art for the synthesis of antibodies, in particular, by chemical synthesis or preferably, by recombinant expression techniques.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with EphA4 (either the full length protein or a domain thereof, e.g., the extracellular domain) and once an immune response is detected, e.g., antibodies specific for EphA4 are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody of the invention wherein, preferably, the hybridoma is generated by fusing splenocytes isolated from a mouse immunized with EphA4 or fragment thereof with myeloma cells and then screening the hybridomas resulting from the fusion for hybridoma clones that secrete an antibody able to bind EphA4.

Antibody fragments which recognize specific EphA4 epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to the EphA4 epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods* 182:41-50; Ames et al., 1995, *J. Immunol. Methods* 184:177; Kettleborough et al., 1994, *Eur. J. Immunol.* 24:952-958; Persic et al., 1997, *Gene* 187:9; Burton et al., 1994, *Advances in Immunology* 57:191-280; International Application No. PCT/GB91/01134; International Publication Nos. WO 90/02809, WO 91/10737, WO 92/01047, WO 92/18619, WO 93/1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

Phage may be screened for EphA4 binding, particularly to the extracellular domain of EphA4. Agonizing EphA4 activity (e.g., increasing EphA4 phosphorylation, reducing EphA4 levels) or cancer cell phenotype inhibiting activity (e.g., reducing colony formation in soft agar or tubular network formation in a three-dimensional basement membrane or extracellular matrix preparation, such as MATRIGEL™) or preferentially binding to an EphA4 epitope exposed on cancer cells but not non-cancer cells (e.g., binding poorly to EphA4 that is bound to ligand in cell-cell contacts while binding well to EphA4 that is not bound to ligand or in cell-cell contacts) may also be screened.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, *BioTechniques* 12:864; Sawai et al., 1995, *AJRI* 34:26; and Better et al., 1988, *Science* 240:1041 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *PNAS* 91:969), and chain shuffling (U.S. Pat. No. 5,565,332).

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, *Nature* 332:323, which are incorporated herein by reference in their entireties).

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *PNAS* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature* 332:323, which are incorporated herein by reference in their entireties.)

Further, the antibodies of the invention can, in turn, be utilized to generate anti-idiotype antibodies using techniques well known to those skilled in the art. (See, e.g., Greenspan & Bona, 1989, *FASEB J.* 7:437-444; and Nissinoff, 1991, *J. Immunol.* 147:2429-2438). The invention provides methods employing the use of polynucleotides comprising a nucleotide sequence encoding an antibody of the invention or a fragment thereof.

5.1.3 Polynucleotides Encoding an Antibody

The methods of the invention also encompass polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. Since the amino acid sequences of the antibodies are known, nucleotide sequences encoding these antibodies can be determined using methods well known in the art, i.e., nucleotide codons known to encode particular amino acids are assembled in such a way to generate a nucleic acid that encodes the antibody or fragment thereof of the invention. Such a polynucleotide encoding the antibody may be assembled from chemically synthesized oligonucleotides (e.g., as described in Kutmeier et al., 1994, *BioTechniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions). Preferably, the polynucleotide generated by the combination of the framework regions and CDRs encodes an antibody that specifically binds to EphA4. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.1.4 Recombinant Expression of an Antibody

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *BioTechnology* 8:2). In a specific embodiment, the expression of nucleotide sequences encoding antibodies or fragments thereof which immunospecifically bind to EphA4 and agonize EphA4, inhibit a cancer cell phenotype, preferentially bind epitopes on EphA4 that are selectively exposed or increased on cancer cells but not non-cancer cells and/or have a $K_{off}$ less than $3 \times 10^{-3}$ s$^{-1}$ is regulated by a constitutive promoter, inducible promoter or tissue specific promoter.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO* 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *PNAS* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, BT483, Hs578T, HTB2, BT2O, NS1 and T47D, NSO (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, *Cell* 11:223), hypoxanthine guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk-, hgprt- or aprt- cells, respectively. Also, antimetabolite resistance can be used as the basis of selection for the following genes: dhfr, which confers resistance to methotrexate (Wigler et al., 1980, *PNAS* 77:357; O'Hare et al., 1981, *PNAS* 78:1527); gpt, which confers resistance to mycophenolic acid (Mulligan & Berg, 1981, *PNAS* 78:2072); neo, which confers resistance to the aminoglycoside G-418 (Wu and Wu, 1991, *Biotherapy* 3:87; Tolstoshev, 1993, *Ann. Rev. Pharmacol. Toxicol.* 32:573; Mulligan, 1993, *Science* 260:926; and Morgan and Anderson, 1993, *Ann. Rev. Biochem.* 62: 191; May, 1993, *TIB TECH* 11: 155-); and hygro, which confers resistance to hygromycin (Santerre et al., 1984, *Gene* 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; and Kohler, 1980, *PNAS* 77:2197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.2 EphA4 Listand Fusion Proteins

The present invention encompasses the use of fusion proteins comprising an EphA4 ligand, for example, example Ephrins A1, A2, A3, A4, A5, B2, and B3; B61, AL1/RAGS, LERK4, Htk-L, and Elk-L3, or a ligand fragment thereof (preferably a fragment that binds to and elicits signaling of EphA4, recombinantly fused or chemically conjugated (including both covalent and non-covalent conjugations) to a heterologous agent, particularly the Fc region of an antibody, to generate a fusion protein (see U.S. Pat. No. 5,116,964, by Capan and Lasky). The heterologous agent may be a polypeptide (or portion thereof, preferably a polypeptide of at least 10, at least 20, at least 30, at least 40, at least 50, at least 60, at least 70, at least 80, at least 90 or at least 100 amino acids), nucleic acid, small molecule (less than 1000 daltons), or other organic compound. The fusion does not necessarily need to be direct, but may occur through linker sequences. Such fusion proteins may be used in vivo to detect, treat, manage, or monitor the progression of a disorder using methods known in the art. In a preferred embodiment, EphA4 ligand-fusion proteins are used as EphA4 agonists.

5.3 Prophylactic/Therapeutic Methods

The present invention encompasses methods for treating, preventing, or managing a disease or disorder associated with overexpression of EphA4 and/or cell hyperproliferative disorders, preferably cancer, in a subject comprising administering one or more EphA4 agonistic antibodies or EphA4 cancer cell phenotype inhibiting antibodies or exposed EphA4 epitope antibodies or EphA4 antibodies that bind EphA4 with a $K_{off}$ less than $3\times10^{-1}s^{-1}$, preferably one or more monoclonal (or antibodies from some other source of a single antibody species) EphA4 agonistic antibodies or EphA4 cancer cell phenotype inhibiting antibodies or exposed EphA4 epitope antibodies or EphA4 antibodies that bind EphA4 with a $K_{off}$ less than $3\times10^{-1}s^{-1}$. In a specific embodiment, the disorder to be treated, prevented, or managed is malignant cancer. In another specific embodiment, the disorder to be treated, prevented, or managed is pre-malignant cancer.

In one embodiment, the antibodies of the invention can be administered in combination with one or more other therapeutic agents useful in the treatment, prevention or management of diseases or disorders associated with EphA4 overexpression, hyperproliferative disorders, and/or cancer. In certain embodiments, one or more EphA4 antibodies of the invention are administered to a mammal, preferably a human, concurrently with one or more other therapeutic agents useful for the treatment of cancer. The term "concurrently" is not limited to the administration of prophylactic or therapeutic agents at exactly the same time, but rather it is meant that the EphA4 antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In other embodiments, the EphA4 antibodies of the invention are administered before, concurrently or after surgery. Preferably the surgery completely removes localized tumors or reduces the size of large tumors. Surgery can also be done as a preventive measure or to relieve pain.

In another specific embodiment, the therapeutic and prophylactic methods of the invention comprise administration of an inhibitor of EphA4 expression, such as but not limited to, antisense nucleic acids specific for EphA4, double stranded EphA4 RNA that mediates RNAi, anti-EphA4 ribozymes, etc. (see Section 5.5 infra) or an agonist of EphA4 activity other than an EphA4 antibody, such as small molecule inhibitors or agonists of EphA4 activity.

In a further embodiment, one or more EphA4 agonistic agents of the invention are administered in combination with one or more EphA2 agonistic agents (see U.S. application Ser. No. 10/436,783 by Kinch et al., filed May 12, 2004).

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* ($56^{th}$ ed., 2002).

5.3.1 Patient Population

The invention provides methods for treating, preventing, and managing a disease or disorder associated with EphA4 overexpression and/or hyperproliferative cell disease, particularly cancer, by administrating to a subject in need thereof a therapeutically or prophylactically effective amount of one or more EphA4 antibodies of the invention. In another embodiment, the EphA4 antibodies of the invention can be administered in combination with one or more other therapeutic agents. The subject is preferably a mammal such as non-primate (e.g., cows, pigs, horses, cats, dogs, rats, etc.) and a primate (e.g., monkey, such as a cynomolgous monkey and a human). In a preferred embodiment, the subject is a human.

Specific examples of cancers that can be treated by the methods encompassed by the invention include, but are not limited to, cancers that over express EphA4. In a further embodiment, the cancer is of an epithelial origin. Examples of such cancers are cancer of the lung, colon, prostate, breast, and skin. Other cancers include cancer of the bladder and pancreas and renal cell carcinoma and melanoma. Additional cancers are listed by example and not by limitation in the following section 5.2.1.1. In particular embodiments, methods of the invention can be used to treat and/or prevent metastasis from primary tumors.

The methods and compositions of the invention comprise the administration of one or more EphA4 antibodies of the invention to subjects/patients suffering from or expected to suffer from cancer, e.g., have a genetic predisposition for a particular type of cancer, have been exposed to a carcinogen, or are in remission from a particular cancer. As used herein, "cancer" refers to primary or metastatic cancers. Such patients may or may not have been previously treated for cancer. The methods and compositions of the invention may be used as a first line or second line cancer treatment. Included in the invention is also the treatment of patients undergoing other cancer therapies and the methods and compositions of the invention can be used before any adverse effects or intolerance of these other cancer therapies occurs. The invention also encompasses methods for administering one or more EphA4 antibodies of the invention to treat or ameliorate symptoms in refractory patients. In a certain embodiment, that a cancer is refractory to a therapy means that at least some significant portion of the cancer cells are not killed or their cell division arrested. The determination of whether the cancer cells are refractory can be made either in vivo or in vitro by any method known in the art for assaying the effectiveness of treatment on cancer cells, using the art-accepted meanings of "refractory" in such a context. In various embodiments, a cancer is refractory where the number of cancer cells has not been significantly reduced, or has increased. The invention also encompasses methods for administering one or more EphA4 agonistic antibodies to prevent the onset or recurrence of cancer in patients predisposed to having cancer.

In particular embodiments, the EphA4 antibodies of the invention, or other therapeutics that reduce EphA4 expression, are administered to reverse resistance or reduced sensitivity of cancer cells to certain hormonal, radiation and chemotherapeutic agents thereby resensitizing the cancer cells to one or more of these agents, which can then be administered (or continue to be administered) to treat or manage cancer, including to prevent metastasis. In a specific embodiment, EphA4 antibodies of the invention are administered to patients with increased levels of the cytokine IL-6, which has been associated with the development of cancer cell resistance to different treatment regimens, such as chemotherapy and hormonal therapy. In another specific embodiment, EphA4 antibodies of the invention are administered to patients suffering from breast cancer that have a decreased responsiveness or are refractory to tamoxifen treatment. In another specific embodiment, EphA4 antibodies of the invention are administered to patients with increased levels of the cytokine IL-6, which has been associated with the development of cancer cell resistance to different treatment regimens, such as chemotherapy and hormonal therapy.

In alternate embodiments, the invention provides methods for treating patients' cancer by administering one or more EphA4 antibodies of the invention in combination with any other treatment or to patients who have proven refractory to other treatments but are no longer on these treatments. In certain embodiments, the patients being treated by the methods of the invention are patients already being treated with chemotherapy, radiation therapy, hormonal therapy, or biological therapy/immunotherapy. Among these patients are refractory patients and those with cancer despite treatment with existing cancer therapies. In other embodiments, the patients have been treated and have no disease activity and one or more agonistic antibodies of the invention are administered to prevent the recurrence of cancer.

In preferred embodiments, the existing treatment is chemotherapy. In particular embodiments, the existing treatment includes administration of chemotherapies including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, etc. Among these patients are patients treated with radiation therapy, hormonal therapy and/or biological therapy/immunotherapy. Also among these patients are those who have undergone surgery for the treatment of cancer.

Alternatively, the invention also encompasses methods for treating patients undergoing or having undergone radiation therapy. Among these are patients being treated or previously treated with chemotherapy, hormonal therapy and/or biological therapy/immunotherapy. Also among these patients are those who have undergone surgery for the treatment of cancer.

In other embodiments, the invention encompasses methods for treating patients undergoing or having undergone hormonal therapy and/or biological therapy/immunotherapy. Among these are patients being treated or having been treated with chemotherapy and/or radiation therapy. Also among these patients are those who have undergone surgery for the treatment of cancer.

Additionally, the invention also provides methods of treatment of cancer as an alternative to chemotherapy, radiation therapy, hormonal therapy, and/or biological therapy/immunotherapy where the therapy has proven or may prove too toxic, i.e., results in unacceptable or unbearable side effects, for the subject being treated. The subject being treated with the methods of the invention may, optionally, be treated with other cancer treatments such as surgery, chemotherapy, radiation therapy, hormonal therapy or biological therapy, depending on which treatment was found to be unacceptable or unbearable.

In other embodiments, the invention provides administration of one or more agonistic monoclonal antibodies of the invention without any other cancer therapies for the treatment of cancer, but who have proved refractory to such treatments. In specific embodiments, patients refractory to other cancer therapies are administered one or more agonistic monoclonal antibodies in the absence of cancer therapies.

In other embodiments, patients with a pre-malignant cancer associated with cells that overexpress EphA4 can be administered antibodies of the invention to treat the disorder and decrease the likelihood that it will progress to malignant cancer. In a specific embodiments, the pre-malignant cancer is high-grade prostatic intraepithelial neoplasia (PIN), ductal carcinoma of the breast in, or compound nevi.

In yet other embodiments, the invention provides methods of treating, preventing and managing non-cancer hyperproliferative cell disorders, particularly those associated with overexpression of EphA4, including but not limited to, asthma, chromic obstructive pulmonary disorder (COPD), restenosis (smooth muscle and/or endothelial), psoriasis, etc. These methods include methods analogous to those described above for treating, preventing and managing cancer, for example, by administering the EphA4 antibodies of the invention, as well as agents that inhibit EphA4 expression, combination therapy, administration to patients refractory to particular treatments, etc.

5.3.1.1. Cancers

Cancers and related disorders that can be treated, prevented, or managed by methods and compositions of the present invention include but are not limited to cancers of an epithelial cell origin. In a preferred embodiment, the cancer is a cancer of the pancreas. Examples of such cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, difflusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America)

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic rnyelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, breast, prostate, bladder, kidney, pancreas, ovary, or uterus. In other specific embodiments, sarcoma, melanoma, or leukemia is treated or prevented.

In some embodiments, the cancer is malignant and overexpresses EphA4. In other embodiments, the cancer is pre-malignant and overexpresses EphA4. In preferred embodiments, the methods and compositions of the invention are used for the treatment and/or prevention of breast, colon, ovarian, lung, and prostate cancers and melanoma and are provided below by example rather than by limitation.

5.3.1.2. Treatment of Breast Cancer

In specific embodiments, patients with breast cancer are administered an effective amount of one or more monoclonal antibodies of the invention. In another embodiment, the antibodies of the invention can be administered in combination with an effective amount of one or more other agents useful for breast cancer therapy including but not limited to: doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), herceptin, tamoxifen, the combination of tamoxifen and cytotoxic chemotherapy, taxanes (such as docetaxel and paclitaxel). In a further embodiment, antibodies of the invention can be administered with taxanes plus standard doxorubicin and cyclophosphamide for adjuvant treatment of node-positive, localized breast cancer.

In a specific embodiment, patients with pre-malignant ductal carcinoma of the breast are administered an EphA4 antibody of the invention to treat the disorder and decrease the likelihood that it will progress to malignant breast cancer.

5.3.1.3. Treatment of Colon Cancer

In specific embodiments, patients with colon cancer are administered an effective amount of one or more monoclonal antibodies of the invention. In another embodiment, the antibodies of the invention can be administered in combination with an effective amount of one or more other agents useful for colon cancer therapy including but not limited to: the combination of 5-Fu and leucovorin, the combination of 5-FU and levamisole, irinotecan (CPT-11) or the combination of irinotecan, 5-FU and leucovorin (IFL).

5.3.1.4. Treatment of Prostate Cancer

In specific embodiments, patients with prostate cancer are administered an effective amount of one or more monoclonal antibodies of the invention. In another embodiment, the antibodies of the invention can be administered in combination with an effective amount of one or more other agents useful for prostate cancer therapy including but not limited to: external-beam radiation therapy, interstitial implantation of radioisotopes (i.e., $I^{125}$, palladium, iridium), leuprolide or other LHRH agonists, non-steroidal antiandrogens (flutamide, nilutamide, bicalutamide), steroidal antiandrogens (cyproterone acetate), the combination of leuprolide and flutamide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxel, paclitaxel, estramustine/docetaxel, estramustine/etoposide, estramustine/vinblastine, and estramustine/paclitaxel.

In a specific embodiment, patients with pre-malignant high-grade prostatic intraepithelial neoplasia (PIN) are administered an EphA4 antibody of the invention to treat the disorder and decrease the likelihood that it will progress to malignant prostate cancer.

5.3.1.5. Treatment of Melanoma

In specific embodiments, patients with melanoma are administered an effective amount of one or more monoclonal antibodies of the invention. In another embodiment, the antibodies of the invention can be administered in combination with an effective amount of one or more other agents useful for melanoma cancer therapy including but not limited to: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2). In a specific embodiment, an effective amount of one or more agonistic monoclonal antibodies of the invention can be administered in combination with isolated hyperthermic limb perfusion (ILP) with melphalan (L-PAM), with or without tumor necrosis factor-alpha (TNF-alpha) to patients with multiple brain metastases, bone metastases, and spinal cord compression to achieve symptom relief and some shrinkage of the tumor with radiation therapy.

In a specific embodiment, patients with pre-malignant compound nevi are administered an EphA4 antibody of the invention to treat the disorder and decrease the likelihood that it will progress to malignant melanoma.

5.3.1.6. Treatment of Ovarian Cancer

In specific embodiments, patients with ovarian cancer are administered an effective amount of one or more monoclonal antibodies of the invention. In another embodiment, the antibodies of the invention can be administered in combination with an effective amount of one or more other agents useful for ovarian cancer therapy including but not limited to: intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. It is contemplated that an effective amount of one or more agonistic monoclonal antibodies of the invention is administered in combination with the administration Taxol for patients with platinum-refractory disease. Included is the treatment of patients with refractory ovarian cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

5.3.1.7. Treatment of Lung Cancers

In specific embodiments, patients with small lung cell cancer are administered an effective amount of one or more monoclonal antibodies of the invention. In another embodiment, the antibodies of the invention can be administered in combination with an effective amount of one or more other agents useful for lung cancer therapy including but not limited to: thoracic radiation therapy, cisplatin, vincristine, doxorubicin, and etoposide, alone or in combination, the combination of cyclophosphamide, doxorubicin, vincristine/etoposide, and cisplatin (CAV/EP), local palliation with endobronchial laser therapy, endobronchial stents, and/or brachytherapy.

In other specific embodiments, patients with non-small lung cell cancer are administered an effective amount of one or more monoclonal antibodies of the invention in combination with an effective amount of one or more other agents useful for lung cancer therapy including but not limited to: palliative radiation therapy, the combination of cisplatin, vinblastine and mitomycin, the combination of cisplatin and vinorelbine, paclitaxel, docetaxel or gemcitabine, the combination of carboplatin and paclitaxel, interstitial radiation therapy for endobronchial lesions or stereotactic radiosurgery.

5.3.2 Other Prophylactic/Therapeutic Agents

In some embodiments, therapy by administration of one or more monoclonal antibodies is combined with the administration of one or more therapies such as, but not limited to, chemotherapies, radiation therapies, hormonal therapies, and/or biological therapies/immunotherapies. Prophylactic/therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including, but not limited to, double-stranded or single-stranded DNA, or double-stranded or single-stranded RNA, as well as triple helix nucleic acid molecules. Prophylavtic/therapeutic agents can be derived from any known organism (including, but not limited to, animals, plants, bacteria, fungi, and protista, or viruses) or from a library of synthetic molecules.

In a specific embodiment, the methods of the invention encompass administration of a therapeutic antibody of the invention in combination with the administration of one or more prophylactic/therapeutic agents that are angiogenesis inhibitors such as, but not limited to: Angiostatin (plasminogen fragment); antiangiogenic antithrombin III; Angiozyme; ABT-627; Bay 12-9566; Benefm; Bevacizumab; BMS-275291; cartilage-derived inhibitor (CDI); CAI; CD59 complement fragment; CEP-7055; Col 3; Combretastatin A-4; Endostatin (collagen XVIII fragment); fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-β); Vasculostatin; Vasostatin (calreticulin fragment); ZD6126; ZD6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflomithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safmgol, safmgol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfm, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, antidorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-aminotriazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, rasGAP inhibitor, retelliptine demethylated, rhenium Re 186 etidronate, rhizoxin, ribozymes, RII retinamide, rogletimide, rohitukine, romurtide, roquinimex, rubiginone B 1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Preferred additional anti-cancer drugs are 5-fluorouracil and leucovorin.

In more particular embodiments, the present invention also comprises the administration of one or more monoclonal antibodies of the invention in combination with the administration of one or more therapies such as, but not limited to anti-cancer agents such as those disclosed in Table 1, preferably for the treatment of breast, ovary, melanoma, prostate, colon and lung cancers as described above.

TABLE 1

| Therapeutic Agent | Administration | Dose | Intervals |
|---|---|---|---|
| doxorubicin hydrochloride (Adriamycin RDF ® and Adriamycin PFS ®) | Intravenous | 60-75 mg/m² on Day 1 | 21 day intervals |
| epirubicin hydrochloride (Ellence ™) | Intravenous | 100-120 mg/m² on Day 1 of each cycle or divided equally and given on Days 1-8 of the cycle | 3-4 week cycles |

TABLE 1-continued

| Therapeutic Agent | Administration | Dose | Intervals |
|---|---|---|---|
| fluorousacil | Intravenous | How supplied: 5 ml and 10 ml vials (containing 250 and 500 mg flourouracil respectively) | |
| docetaxel (Taxotere ®) | Intravenous | 60-100 mg/m$^2$ over 1 hour | Once every 3 weeks |
| paclitaxel (Taxol ®) | Intravenous | 175 mg/m$^2$ over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 ml or 20 unit mark) | Once a day |
| flutamide (Eulexin ®) | Oral (capsule) | 250 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/ml | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 ml of 20 mg/ml solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | How supplied: solution of 1 mg/ml in multi-dose vials of 50 mL and 100 mL | |
| mitomycin | Injection | supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule-administration intravenously at 1000 mg/m$^2$ over 30 minutes on 3 week schedule-Gemzar administered intravenously at 1250 mg/m$^2$ over 30 minutes | 4 week schedule-Days 1, 8 and 15 of each 28-day cycle. Cisplatin intravenously at 100 mg/m$^2$ on day 1 after the infusion of Gemzar. 3 week schedule-Days 1 and 8 of each 21 day cycle. Cisplatin at dosage of 100 mg/m$^2$ administered intravenously after administration of Gemzar on day 1. |

TABLE 1-continued

| Therapeutic Agent | Administration | Dose | Intervals |
| --- | --- | --- | --- |
| carboplatin (Paraplatin ®) | Intravenous | Single agent therapy: 360 mg/m² I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m² daily | 5 consecutive days Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |

The invention also encompasses administration of the EphA4 antibodies of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physician's Desk Reference* (56th ed., 2002).

5.4 Identification of Antibodies of the Invention

5.4.1 Agonistic Antibodies

Antibodies of the invention may preferably agonize (i.e., elicit EphA4 phosphorylation) as well as immunospecifically bind to the EphA4 receptor. When agonized, EphA4 phosphorylates a 75 kDa EphA4-associated protein and may itself be phosphorylated and then subsequently degraded. Any method known in the art to assay either the level of EphA4 or 75 kDa EphA4-associated protein phosphorylation, activity, or expression can be used to assay candidate EphA4 antibodies to determine their agonistic activity (see, e.g., Section 6.2 infra).

5.4.2 Antibodies that Preferentially Bind EphA4 Epitopes Exposed on Cancer Cells Antibodies of the invention may preferably bind to EphA4 epitopes exposed on cancer cells (e.g., cells overexpressing EphA4 and/or cells with substantial EphA4 that is not bound to ligand) but not non-cancer cells or cells where EphA4 is bound to ligand. In this embodiment, antibodies of the invention are antibodies directed to an EphA4 epitope not exposed on non-cancer cells but exposed on cancer cells.

Any method known in the art to determine candidate EphA4 antibody binding/localization on a cell can be used to screen candidate antibodies for desirable binding properties. In a one embodiment, immunofluorescence microscopy is used to determine the binding characteristics of an antibody. Standard techniques can be used to compare the binding of an antibody binding to cells grown in vitro. In a specific embodiment, antibody binding to cancer cells is compared to antibody binding to non-cancer cells. An exposed EphA4 epitope antibody binds poorly to non-cancer cells but binds well to cancer cells. In another specific embodiment, antibody binding to non-cancer dissociated cells (e.g., treated with a calcium chelator such as EGTA) is compared to antibody binding to non-cancer cells that have not been dissociated. An exposed EphA4 epitope antibody binds poorly non-cancer cells that have not been dissociated but binds well to dissociated non-cancer cells.

In another embodiment, flow cytometry is used to determine the binding characteristics of an antibody. In this embodiment, EphA4 may or may not be crosslinked to its ligand. An exposed EphA4 epitope antibody binds poorly crosslinked EphA4 but binds well to uncrosslinked EphA4.

In another embodiment, cell-based or immunoassays are used to determine the binding characteristics of an antibody. In this embodiment, antibodies that can compete with an EphA4 ligand (e.g., Ephrins A1, A2, A3, A4, AS, B2, and B3; B61, AL1/RAGS, LERK4, Htk-L, and Elk-L3) for binding to EphA4 displace the ligand from EphA4. The EphA4 ligand used in this assay can be soluble protein (e.g., recombinantly expressed) or expressed on a cell so that it is anchored to the cell.

5.4.3 Cancer Cell Phenotype Inhibiting Antibodies

Antibodies of the invention may preferably inhibit (and preferably reduce) cancer cell colony formation in, for example, soft agar, or tubular network formation in a three-dimensional basement membrane or extracellular matrix preparation as well as immunospecifically bind to the EphA4 receptor. One of skill in the art can assay candidate EphA4 antibodies for their ability to inhibit such behavior (see, e.g., Section 6.3 infra). Metastatic tumor cells suspended in soft agar form colonies while benign tumors cells do not. Colony formation in soft agar can be assayed as described in Zelinski et al. (2001, *Cancer Res.* 61:2301-6, incorporated herein by reference in its entirety). Antibodies to be assayed for agonistic activity can be included in bottom and top agar solutions. Metastatic tumor cells can be suspended in soft agar and allowed to grow. EphA4 cancer cell phenotype inhibiting antibodies will inhibit colony formation.

Another behavior specific to metastatic cells that can be used to identify cancer cell phenotype inhibiting antibodies is tubular network formation within a three-dimensional microenvironment, such as MATRIGEL™. Normally, cancer cells quickly assemble into tubular networks that progressively invade all throughout the MATRIGEL™. In the presence of an EphA4 cancer cell phenotype inhibiting antibody, cancer cells assemble into spherical structures that resemble the behavior of differentiated, non-cancerous cells. Accordingly, EphA4 cancer cell phenotype inhibiting antibodies can be identified by their ability to inhibit tubular network formation of cancer cells.

Any other method that detects an increase in contact inhibition of cell proliferation (e.g., reduction of colony formation in a monolayer cell culture) may also be used to identify cancer cell phenotype inhibiting antibodies.

In addition to inhibiting cancer cell colony formation, cancer cell phenotype inhibiting antibodies may also cause a reduction or elimination of colonies when added to already established colonies of cancer cells by cell killing, e.g., by necrosis or apoptosis. Methods for assaying for necrosis and apoptosis are well known in the art.

5.4.4 Antibodies with Low $K_{off}$ Rates

The binding affinity of a monoclonal antibody of the invention to EphA4 or a fragment thereof and the off-rate of a monoclonal antibody-EphA4 interaction can be determined by competitive binding assays. One example of a competitive binding assay is a radioimmunoassay comprising the incubation of labeled EphA4 (e.g., $^3H$ or $^{125}I$) with the monoclonal antibody of interest in the presence of increasing amounts of unlabeled EphA4, and the detection of the monoclonal antibody bound to the labeled EphA4. The affinity of a monoclonal antibody for an EphA4 and the binding off-rates can be determined from the data by scatchard plot analysis. Competition with a second monoclonal antibody can also be determined using radioimmunoassays. In this case, EphA4 is incubated with a monoclonal antibody conjugated to a labeled compound (e.g., $^3H$ or $^{125}I$) in the presence of increasing amounts of a second unlabeled monoclonal antibody.

In a preferred embodiment, a candidate EphA4 antibody may be assayed using any surface plasmon resonance based assays known in the art for characterizing the kinetic parameters of the EphA4-EphA4 antibody interaction. Any SPR instrument commercially available including, but not limited to, BIACORE Instruments, available from Biacore AB (Uppsala, Sweden); IAsys instruments available form Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution. SPR is based on measuring the change in refractive index of the solvent near the surface that occurs upon complex formation or dissociation. The surface onto which the immobilization occur is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to direct covalent coupling via amine groups, direct covalent coupling via sulfhydryl groups, biotin attachment to avidin coated surface, aldehyde coupling to carbohydrate groups and attachment through the histidine tag with NTA chips.

In a more preferred embodiment, BIACORE™ kinetic analysis is used to determine the binding on and off rates of monoclonal antibodies to EphA4 (see, e.g., Section 6.5 infra). BIACORE™ kinetic analysis comprises analyzing the binding and dissociation of a monoclonal antibody from chips with immobilized EphA4 or fragment thereof on their surface.

Once an entire data set is collected, the resulting binding curves are globally fitted using computer algorithms supplied by the manufacturer, BIAcore, Inc. (Piscataway, N.J.). These algorithms calculate both the $K_{on}$ and $K_{off}$ from which the apparent equilibrium binding constant, $K_D$ is deduced as the ratio of the two rate constants (i.e., $K_{off}/K_{on}$) More detailed treatments of how the individual rate constants are derived can be found in the BIAevaluaion Software Handbook (BIAcore, Inc., Piscataway, N.J.). The analysis of the generated data may be done using any method known in the art. For a review of the various methods of interpretation of the kinetic data generated see Myszka, 1997, *Current Opinion in Biotechnology* 8: 50-7; Fisher et al., 1994, *Current Opinion in Biotechnology* 5: 389-95; O'Shannessy, 1994, *Current Opinion in Biotechnology*, 5:65-71; Chaiken et al., 1992, *Analytical Biochemistry*, 201: 197-210; Morton et al., 1995, *Analytical Biochemistry* 227: 176-85; O'Shannessy et al., 1996, *Analytical Biochemistry* 236: 275-83; all of which are incorporated herein by reference in their entirety.

An antibody that immunospecifically binds to EphA4 preferably has a $$K_{off} \text{ rate} \Big( \text{antibody}(Ab) + \text{antigen}(Ag) \xrightarrow{K_{off}} Ab\text{-}Ag \Big)$$

of less than $3 \times 10^{-3}$ $s^{-1}$, less than $10^{-3}$ $s^{-1}$, less than $10^{-4}$ $s^{-1}$, less than $5 \times 10^{-4}$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than $10^{-7}$ $s^{-1}$, less than $5 \times 10^{-7}$ $s^{-1}$, less than $10^{-8}$ $s^{-1}$, less than $5 \times 10^{-8}$ $s^{-1}$, less than $10^{-9}$ $s^{-1}$, less than $5 \times 10^{-9}$ $s^{-1}$, or less than $10^{-10}$ $s^{-1}$.

Thus, the invention provides methods of assaying and screening for EphA4 antibodies of the invention by incubating antibodies that specifically bind EphA4, particularly that bind the extracellular domain of EphA4, with cells that express EphA4, particularly cancer cells, preferably metastatic cancer cells, that overexpress EphA4 (relative to non-cancer cells of the same cell type) and then assaying for an increase in EphA4 phosphorylation and/or EphA4 degradation (for agonistic antibodies), or reduction in colony formation in soft agar or tubular network formation in three-dimensional basement membrane or extracellular matrix preparation (for cancer cell phenotype inhibiting antibodies), or increased antibody binding to cancer cells as compared to non-cancer cells by e.g., immunofluorescence (for exposed EphA4 epitope antibodies) thereby identifying an EphA4 antibody of the invention.

5.5 Nucleic Acid Molecules

In addition to EphA4 antibodies of the invention, nucleic acid molecules specific for EphA4 can also be used to decrease EphA4 expression and, therefore, be used in methods of the invention.

5.5.1 Antisense

The present invention encompasses antisense nucleic acid molecules, i.e., molecules which are complementary to all or part of a sense nucleic acid encoding EphA4, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine; 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, i.e., EphA4).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, *Nucleic Acids Res.* 15:6625). The antisense nucleic acid molecule can also comprise a 2'-o-methylribonucleotide (Inoue et al., 1987, *Nucleic Acids Res.* 15:6131) or a chimeric RNA-DNA analogue (Inoue et al., 1987, *FEBS Lett.* 215:327).

5.5.2 Ribozymes

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes; described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding EphA4 can be designed based upon the nucleotide sequence of EphA4. For example, a derivative of a Tetrahymena L-19 IVS RNA can be constructed in which the nucleotide sequence of the active site is complementary to the nucleotide sequence to be cleaved in U.S. Pat. Nos. 4,987,071 and 5,116,742. Alternatively, an mRNA encoding a polypeptide of the invention can be used to select a catalytic RNA having a specific ribonuclease activity from a pool of RNA molecules. See, e.g., Bartel and Szostak, 1993, *Science* 261:1411.

5.4.3 RNA Interference

In certain embodiments, an RNA interference (RNAi) molecule is used to decrease EphA4 expression. RNA interference (RNAi) is defined as the ability of double-stranded RNA (dsRNA) to suppress the expression of a gene corresponding to its own sequence. RNAi is also called post-transcriptional gene silencing or PTGS. Since the only RNA molecules normally found in the cytoplasm of a cell are molecules of single-stranded mRNA, the cell has enzymes that recognize and cut dsRNA into fragments containing 21-25 base pairs (approximately two turns of a double helix and which are referred to as small interfering RNA or siRNA). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time.

Double-stranded (ds) RNA can be used to interfere with gene expression in mammals (Wianny & Zernicka-Goetz, 2000, *Nature Cell Biology* 2: 70-75; incorporated herein by reference in its entirety). dsRNA is used as inhibitory RNA or RNAi of the function of EphA4 to produce a phenotype that is the same as that of a null mutant of EphA4 (Wianny & Zernicka-Goetz, 2000, *Nature Cell Biology* 2: 70-75).

5.6 Characterization and Demonstration of Therapeutic or Prophylactic Utility

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice where a mouse EphA4 is replaced with the human EphA4, nude mice with human xenografts, animal models, such as hamsters, rabbits, etc. known in the art and described in *Relevance of Tumor Models for Anticancer Drug Development* (1999, eds. Fiebig and Burger); *Contributions to Oncology* (1999, Karger); *The Nude Mouse in Oncology Research* (1991, eds. Boven and Winograd); and *Anticancer Drug Development Guide* (1997 ed. Teicher), herein incorporated by reference in their entireties.

5.6.1 Demonstration of Therapeutic or Prophylactic Utility

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed, e.g., increased phosphorylation or degradation of EphA4, inhibition of or decrease in growth and/or colony formation in soft agar or tubular network formation in three-dimensional basement membrane or extracellular matrix preparations. A lower level of proliferation or survival of the contacted cells indicates that the therapeutic agent is effective to treat the condition in the patient. Alternatively, instead of culturing cells from a patient, therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, increased phosphorylation or degradation of EphA4, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer.

5.7 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more EphA4 antibodies of the invention and a pharmaceutically acceptable carrier or an agent that reduces EphA4 expression (e.g., antisense oligonucleotides) and a pharmaceutically acceptable carrier. In a further embodiment, the composition of the invention further comprises an additional therapeutic, e.g., anti-cancer, agent.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer an agonistic monoclonal antibody of the invention or the combination of an agonistic monoclonal antibody of the invention and a prophylactic agent or therapeutic agent useful for preventing or treating cancer, e.g., encapsulation in liposomes, microparticles, microcapsules, recombinant cells capable of expressing the antibody or antibody fragment, receptor-mediated endocytosis (see, e.g., Wu and Wu, 1987, *J. Biol. Chem.* 262:4429-4432), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural, and mucosal (e.g., intranasal, inhaled, and oral routes). In a specific embodiment, prophylactic or therapeutic agents of the invention are administered intramuscularly, intravenously, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In yet another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105); U.S. Pat. Nos. 5,679,377; 5,916,597; 5,912,015; 5,989,463; 5,128,326; International Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

5.7.1 Gene Therapy

In a specific embodiment, nucleic acids that reduce EphA4 expression (e.g., EphA4 antisense nucleic acids or EphA4 dsRNA) are administered to treat, prevent or manage cancer by way of gene therapy. Gene therapy refers to therapy performed by the administration to a subject of an expressed or expressible nucleic acid. In this embodiment of the invention, the antisense nucleic acids are produce and mediate a prophylactic or therapeutic effect.

Any of the methods for gene therapy available in the art can be used according to the present invention. Exemplary methods are described below.

For general reviews of the methods of gene therapy, see Goldspiel et al., 1993, *Clinical Pharmacy* 12:488; Wu and Wu, 1991, *Biotherapy* 3:87; Tolstoshev, 1993, *Ann. Rev. Pharmacol. Toxicol.* 32:573; Mulligan, 1993, *Science* 260: 926-932; and Morgan and Anderson, 1993, *Ann. Rev. Biochem.* 62:191; May, 1993, *TIBTECH* 11:155. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises EphA4 nucleic acids that reduce EphA4 expression, said nucleic acids being part of an expression vector that expresses the nucleic acid in a suitable host. In particular, such nucleic acids have promoters, preferably heterologous promoters, said promoter being inducible or constitutive, and, optionally, tissue-specific. In another particular embodiment, nucleic acid molecules are used in which the nucleic acid that reduces EphA4 expression and any other desired sequences are flanked by regions that promote homologous recombination at a desired site in the genome, thus providing for intrachromosomal expression of the nucleic acids that reduce EphA4 expression (Koller and Smithies, 1989, *PNAS* 86:8932; Zijlstra et al., 1989, *Nature* 342:435).

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy. In a specific embodiment, the nucleic acid sequences are directly administered in vivo. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J. Biol. Chem.* 262:4429) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180; WO 92/22635; WO92/203 16; WO93/14188, WO 93/20221). Alternatively, the nucleic acid can be introduced intracellularly and incorporated within host cell DNA for expression, by homologous recombination (Koller and Smithies, 1989, *PNAS* 86:8932; and Zijlstra et al., 1989, *Nature* 342:435).

In a specific embodiment, viral vectors that contain the nucleic acid sequences that reduce EphA4 expression are used. For example, a retroviral vector can be used (see Miller et al., 1993, *Meth. Enzymol.* 217:581). These retroviral vectors contain the components necessary for the correct packaging of the viral genome and integration into the host cell DNA. The nucleic acid sequences to be used in gene therapy are cloned into one or more vectors, which facilitates delivery of the nucleic acid into a subject. More detail about retroviral vectors can be found in Boesen et al., 1994, *Biotherapy* 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, *J. Clin. Invest.* 93:644-651; Klein et al., 1994, *Blood* 83:1467-1473; Salmons and Gunzberg, 1993, *Human Gene Therapy* 4:129-141; and Grossman and Wilson, 1993, *Curr. Opin. in Genetics Devel.* 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Adenoviruses have the advantage of being capable of infecting non-dividing cells. Kozarsky and Wilson, 1993, *Current Opinion in Genetics Development* 3:499 present a review of adenovirus-based gene therapy. Bout et al., 1994, *Human Gene Therapy* 5:3-10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431; Rosenfeld et al., 1992, *Cell* 68:143; Mastrangeli et al., 1993, *J. Clin. Invest.* 91:225; International Publication No. WO94/12649; and Wang et al., 1995, *Gene Therapy* 2:775. In a preferred embodiment, adenovirus vectors are used.

Adeno-associated virus (AAV) has also been proposed for use in gene therapy (Walsh et al., 1993, *Proc. Soc. Exp. Biol. Med.* 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, 1993, *Meth. Enzymol.* 217:599; Cohen et al., 1993, *Meth. Enzymol.* 217:618) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. The amount of cells envisioned for use depends on the desired effect, patient state, etc., and can be determined by one skilled in the art.

5.7.2 Formulations

Pharmaceutical compositions for use in accordance with the present invention may be formulated in conventional manner using one or more physiologically acceptable carriers or excipients.

Thus, the EphA4 agonistic antibodies of the invention or other anti-EphA4 agents (e.g., antisense and other nucleic acids) and their physiologically acceptable salts and solvates may be formulated for administration by inhalation or insufflation (either through the mouth or the nose) or oral, parenteral or mucosal (such as buccal, vaginal, rectal, sublingual) administration. In a preferred embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the prophylactic or therapeutic agents for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The prophylactic or therapeutic agents may also be formulated in rectal compositions such as suppositories or retention enemas, e.g., containing conventional suppository bases such as cocoa butter or other glycerides.

In addition to the formulations described previously, the prophylactic or therapeutic agents may also be formulated as a depot preparation. Such long acting formulations may be administered by implantation (for example subcutaneously or intramuscularly) or by intramuscular injection. Thus, for example, the prophylactic or therapeutic agents may be formulated with suitable polymeric or hydrophobic materials (for example as an emulsion in an acceptable oil) or ion exchange resins, or as sparingly soluble derivatives, for example, as a sparingly soluble salt.

The invention also provides that a prophylactic or therapeutic agent is packaged in a hermetically sealed container such as an ampoule or sachette indicating the quantity. In one embodiment, the prophylactic or therapeutic agent is supplied as a dry sterilized lyophilized powder or water free concentrate in a hermetically sealed container and can be reconstituted, e.g., with water or saline to the appropriate concentration for administration to a subject.

In a preferred embodiment of the invention, the formulation and administration of various chemotherapeutic, biological/immunotherapeutic and hormonal therapeutic agents are known in the art and often described in the *Physician's Desk Reference*, 56$^{th}$ ed. (2002). For instance, in certain specific embodiments of the invention, the therapeutic agents of the invention can be formulated and supplied as provided in Table 1.

In other embodiments of the invention, radiation therapy agents such as radioactive isotopes can be given orally as liquids in capsules or as a drink. Radioactive isotopes can also be formulated for intravenous injections. The skilled oncologist can determine the preferred formulation and route of administration.

In certain embodiments the agonistic monoclonal antibodies of the invention, are formulated at 1 mg/ml, 5 mg/ml, 10 mg/ml, and 25 mg/ml for intravenous injections and at 5 mg/ml, 10 mg/ml, and 80 mg/ml for repeated subcutaneous administration and intramuscular injection.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.7.3 Dosages

The amount of the composition of the invention which will be effective in the treatment, prevention or management of cancer can be determined by standard research techniques. For example, the dosage of the composition which will be effective in the treatment, prevention or management of cancer can be determined by administering the composition to an animal model such as, e.g., the animal models disclosed herein or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors which will be known to one of ordinary skill in the art. Such factors include the disease to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the cancer, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible.

For other cancer therapeutic agents administered to a patient, the typical doses of various cancer therapeutics known in the art are provided in Table 1. Given the invention, certain preferred embodiments will encompass the administration of lower dosages in combination treatment regimens than dosages recommended for the administration of single agents.

The invention provides for any method of administrating lower doses of known prophylactic or therapeutic agents than previously thought to be effective for the prevention, treatment, management or amelioration of cancer. Preferably, lower doses of known anti-cancer therapies are administered in combination with lower doses of agonistic monoclonal antibodies of the invention.

5.8 Kits

The invention provides a pharmaceutical pack or kit comprising one or more containers filled with an monoclonal antibody of the invention. Additionally, one or more other prophylactic or therapeutic agents useful for the treatment of a cancer can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more a monoclonal antibodies of the invention. In another embodiment, a kit further comprises one or more other prophylactic or therapeutic agents useful for the treatment of cancer, in one or more containers. In certain embodiments, the other prophylactic or therapeutic agent is a chemotherapeutic. In other embodiments, the prophylactic or therapeutic agent is a biological or hormonal therapeutic.

6. EXAMPLES

6.1 EphA4 Antibodies Cause Changes in Cell Behavior

Cell Adhesion and Cell Rounding Assays

To examine cell rounding, pancreatic cancer cell line Aspc1 cells were plated onto six-well dishes previously coated with extracellular membrane (ECM) proteins, or plated onto ECM protein-coated coverslips in 24-well dishes. Cells were allowed to adhere for 48 hours, then incubated with media containing EphA4 scFv antibody at 37° C. As a control, sets of cells plated and allowed to adhere as above were incubated with EphA4 scFv antibody at 0° C. rather than 37° C. Following incubation, the EphA4-scFv incubated cells were washed and treated with anti-Flag antibodies to crosslink EphA4-bound scFv. Plates or coverslips were washed, fixed, stained, and visualized by microscopy. Cells incubated with EphA4 antibody at 37° C. show cell rounding relative to cells incubated with EphA4 antibody at 0° C., i.e. a temperature at which the cells will not change shape (FIGS. 1A,B). This further indicates that anti-EphA4 antibodies cause decreased attachment to the ECM matrix. Decreased ECM-cell attachment is significant since these types of adhesions are sites of intracellular signaling that promote cell growth, survival, migration and invasion (Burridge and Chrzanowska-Wodnicka, *Annu. Rev. Cell Dev. Biol.*, 12: 463, 1996; Parsons, *Curr. Opin. Cell Biol.*, 8:146, 1996).

Cell adhesion and cell rounding assays can also be performed as described in Miao, et al. (*Nature Cell Biol.* 2:62, 2000), which is incorporated by reference herein in its entirety. To study cell adhesion, briefly, cells are plated in triplicate onto 96-well plates previously coated with various ECM proteins or poly-L-lysine. Cells are plated at a density of $1\times10^5$ cells per well in the presence or absence of EphA4 antibodies (or other EphA4 agonist) and allowed to adhere for 30 minutes at 37° C. Non-adherent cells are washed from the wells, and adherent cells are fixed, stained, and quantified by measuring absorbance on an enzyme-linked immunosorbent assay (ELISA) reader. Cells treated with EphA4 antibodies show decreases in attachment to ECM protein-treated wells relative to control cells allowed to adhere in the absence of EphA4 antibodies.

For cell rounding assays, briefly, cells are plated onto ECM protein-coated six-well dishes, or ECM protein-coated coverslips in 24-well dishes. Cells are allowed to adhere for 48 hours, then treated with media with or without EphA4 antibody (or other EphA4 agonist) for 10 minutes. Plates or coverslips are washed, fixed, stained, and visualized by microscopy. Cells treated with EphA4 antibody show cell rounding relative to cells treated with media lacking EphA4 antibody, indicating decreased attachment to the ECM matrix.

6.2 Preparation of Monoclonal Antibodies

Immunization and Fusion

Monoclonal antibodies against the extracellular domain of EphA4 are generated using the fusion protein EphA4-Fc. This fusion protein consists of the extracellular domain of human EphA4 linked to human immunoglobulin to facilitate secretion of the fusion protein.

Mice (either Balb/c mice or SJL mice) are injected with 5 µg of EphA4 fusion protein in TiterMax Adjuvant (total volume 100 µl) in the left metatarsal region at days 0 and 7. Mice are injected with 10 µg of EphA4 fusion protein in PBS (total volume 100 µl) in the left metatarsal region at days 12 and 14. On day 15, the popliteal and inguinal lymph node cells from the left leg and groin are removed and somatically fused (using PEG) with P3XBc1-2-13 cells.

Hybridomas producing EphA4 antibody are isolated from fusions of lymph nodes from immunized SJL mice.

Antibody Screening

Supernatants from bulk culture hybridomas can be screened for immunoreactivity against EphA4 using standard molecular biological techniques (e.g., ELISA immunoassay). Supernatants are further screened for the ability to inhibit an EphA4 monoclonal antibody from binding to EphA4. Briefly, the ability of labeled EphA4 antibody to bind EphA4 fusion protein is assayed by competitive ELISA in presence of either unlabeled EphA4 antibody or other unlabeled EphA4 binding protein. These may decrease the amount of labeled EA4 binding to EphA4-Fc with increasing concentrations of unlabeled antibody or binding protein added.

6.3 Use of EphA4 Antibodies

6.3.1 EphA4 Phosphorylation

EphA4 antibodies promoted tyrosine phosphorylation in ASPC1 cells. Cells were incubated in the presence of an anti-EphA4 monoclonal antibody (NED 154-567) or control for 15 minutes at 37° C. Cell lysates were then immunoprecipitated with EphrinA4-Fc (R&D Systems; Minneapolis, Minn.), resolved by SDS-PAGE, and subjected to western blot analysis with a cocktail of the anti-phosphotyrosine antibodies 4G10 (Upstate Biotechnology; Lake Placid N.Y.) and PY20 (BD Transduction Laboratories; Franklin Lakes, N.J.). Increased EphA4 phosphorylation was seen following treatment with EphA4 antibodies, indicating that the EphA4 antibodies agonize EphA4 and likely promote EphA4 auto-phosphorylation.

EphA4 scFv antibody clone EA44 strongly promoted tyrosine phosphorylation of EphA4 (FIG. 6). Cells that express the anti-EphA4 scFv EA44 have been deposited with the American Type Culture Collection (P.O. Box 1549, Manassas, Va. 20108) on Jun. 1, 2004 under the provisions of the Budapest Treaty on the International Recognition of the Deposit of Microorganisms for the Purposes of Patent Procedures, and assigned accession number PTA-6044. The VH and VL CDR amino acid sequences of EA44 are contained in SEQ IDs NO: 22, 24, 26, 28, 30, and 32 respectively (FIG. 7). Aspc1 pancreatic carcinoma cells were incubated with the indicated anti-EphA4 scFv (5 µg/ml) on ice. After 30 minutes, medium was removed, cells were washed with ice-cold PBS, and medium containing 10 µg/ml antibody specific for the flag epitope M2 were placed onto cells. At this time, a control sample was treated with 10 µg/ml mAb9, an antibody known to induce EphA4 tyrosine phosphorylation. Cells were incubated with scFv clones 8, 18, 20, 36, 41, or 44, or mAb9 for 15 minutes at 37° C., washed with ice-cold PBS, and then lysed in Tris-buffered saline containing 1% Triton X-100. EphA4 was immunoprecipitated from the cell lysates using ephrinA4-Fc (4 µg; R&D Systems), resolved by SDS-PAGE, and transferred to nitrocellulose. The status of EphA4 tyrosine phosphorylation was analyzed by western blot analysis using the anti-pTyr antibodies, 4G10 and PY20. As seen in FIG. 6, scFv clone 44 strongly promotes EphA4 phosphorylation.

EphA4 antibodies also promoted tyrosine phosphorylation of an EphA4-associated protein. Cells were incubated with LX13 scFv antibody, washed, and subsequently incubated with anti-Flag antibodies to crosslink scFv on the surface of cells. EphA4 was then immunoprecipitated with EphrinA4-Fc, and western blotting was performed with anti-phosphotyrosine antibodies. As seen in FIG. 2, crosslinking of EphA4 ("X-linked EphA4" lane) causes increased tyrosine phosphorylation of an EphA4-associated protein of approximately 75 kDa relative to phosphorylation of this EphA4-associated protein of approximately 75 kDa in cells in which EphA4 is not crosslinked ("Control" lane).

6.3.2. EphA4 Degradation

Antibody-mediated degradation of EphA4 can also be assessed. Monolayers of EphA4-positive cells, such as the pancreatic carcinoma cell lines ASPC1 or MiaPaca2, are incubated in the presence of EphA4 antibodies (10 µg/ml) at 37° C. Cells are then lysed in Tris-buffered saline containing 1% Triton X-100 (Sigma, St. Louis, Mo.) at the following timepoints after addition of antibody: 0, 0.5. 1, 2, 4, 8, and 24 hours. After measuring protein concentrations (BioRad, Hercules, Calif.), equal quantities of total protein are resolved by SDS-PAGE and transferred to nitrocellulose (Protran™, Schleicher and Schuell, Keene, N.H.). EphA4 levels are visualized via western blot analysis using a commercially available EphA4/Sek monoclonal antibody (BD Biosciences, San Jose, Calif.). Membranes are then stripped and reprobed with a paxillin-specific antibody (clone 5H11; Upstate Biotechnology, Lake Placid, N.Y.) to assure equal loading of total protein between samples.

6.3.3. Growth in Soft Agar

The ability of the antibodies of the invention to inhibit cancer cell formation in soft agar was assayed (such assays may be carried out, e.g., as described in Zelinski et al., 2001, *Cancer Res.* 61:2301, incorporated by reference herein in its entirety). Briefly, cells were suspended in soft agar for 7 days at 37° C in the presence of anti-EphA4 LX13 scFv antibody (LX13), or control solution (PBS). Following incubation with LX13 or PBS, cells were washed and incubated with either an anti-LX13 secondary monoclonal antibody (secondary mab) or PBS. Colony formation was scored microscopically. Clusters containing at least three cells were scored as a positive. As seen in FIG. 3, cells incubated with LX13 and secondary mab ("LX13 bival"), which contain aggregated EphA4, show significant inhibition of growth in soft agar relative to cells incubated with PBS followed by secondary mab alone ("Control") or cells treated with LX13 followed by PBS ("LX13").

The ability of the antibodies of the invention to eliminate cancer cell colonies already formed in soft agar is assayed. Assay methods are similar to those described above except that antibodies are not added to the cancer cells until the third day of growth in soft agar.

6.3.4. Estrogen Dependence in Breast Cancer Cells

Estrogen-sensitive breast cancer cells, MCF-7 cells, were transfected with and stably overexpress human EphA4 (MCF-7$^{EphA4}$). Western blot analyses confirm the ectopic overexpression of EphA4 in transfected cells relative to matched controls (data not shown). Two EphA4-overexpressing clones, EphA4-2 and EphA4-3, were selected for further study.

EphA4 overexpression increases malignant growth and decreases the effect of estrogen. Colony formation in soft agar of the EphA4-2 and EphA4-3 clones and vector alone control were assayed in the presence or absence of estrogen.

In the presence of estrogen, the EphA4-2 and EphA4-3 cells demonstrate a greater than two-fold increase in colony formation in soft agar relative to matched controls (FIG. 4, "+Estrogen"). EphA4-2 and EphA4-3 cells form an average of 4.6 colonies/field (FIG. 4, "+Estrogen", "EphA4-2" and "EphA4-3" bars), while control cells transfected with empty vector form fewer than 2 colonies/field (FIG. 4, "+Estrogen", "Vector" bar).

Parallel studies are performed in the absence of exogenous estrogen (FIG. 4, "−Estrogen" bars). Experimental deprivation of estrogen amplifies differences between the cellular behaviors of control and EphA4-2 and EphA4-3 cells. Although MCF-7 control cells are largely unable to colonize soft agar (FIG. 4, "Vector" bar in "−Estrogen" field, <1 colony/field), EphA4-2 and EphA4-3 cells form more numerous colonies (3.4 colonies/field; FIG. 4, "−Estrogen" bars). While EphA4-2 and EphA4-3 cells colonize soft agar more efficiently than matched controls, these cells grow well in the absence of exogenous estrogen (FIG. 4, "−Estrogen" bars). Thus, EphA4 overexpression decreases the need for exogenous estrogen.

6.3.5. Tubular Network Formation in MATRIGEL™

Tumor cell behavior within a three-dimensional microenvironment, such as MATRIGEL™, can reliably predict the differentiation state and aggressiveness of breast epithelial cells. Monolayer cultures of benign (MCF-10A) or malignant (MDA-MB-231) breast epithelial cells are incubated on MATRIGEL™ in the presence of EphA4 antibodies (10 µg/ml) or control solution (PBS). The behavior of cells on MATRIGEL™ is analyzed as described in Zelinski et al. (2001, *Cancer Res.* 61:2301-6). Briefly, tissue culture dishes are coated with MATRIGEL™ (Collaborative Biomedical Products, Bedford, Mass.) at 37° C. before adding 1×10$^5$ MDA-MB-231 or MCF-10A cells previously incubated on ice for 1 hour with the EphA4 antibody or control solution (PBS). Cells are incubated on MATRIGEL™ for 24 hours at 37° C., and cell behavior is assessed using an Olympus IX-70 inverted light microscope. All images are recorded onto 35 mm film (T-Max-400. Kodak, Rochester, N.Y.).

6.3.6. Growth in vivo

The ability of the antibodies of the invention to inhibit tumor cancer growth in vivo is assayed. Briefly, MDA-MB-231 breast cancer cells are implanted subcutaneously into athymic mice. After the tumors have grown to an average volume of 100 mm$^3$, mice are administered 6 mg/ml EphA4 antibody or PBS control in traperitoneally twice a week for 3 weeks. Tumor growth is assessed and expressed as a ratio of the tumor volume divided by initial tumor volume (100 mm$^3$). Tumor growth is allowed to proceed until tumor volume reaches 1000 mm$^3$. Survival of the mice is assessed by scoring the percent of mice living each day post treatment.

Since receptor tyrosine kinases frequently regulate cellular behaviors that are aberrant in tumors, EphA4 may provide a potential therapeutic target for the antibody-based treatment of pancreatic cancer. Antibody-mediated aggregation of another Eph receptor family member, EphA2, decreases malignant potential of cancer cells (reviewed in Kinch and Carles-Kinch, *Clinical and Experimental Metastasis*, 20:59, 2003). To test if EphA4-targeting would result in a similar outcome, several scFv fragments that bind human EphA4 were tested. EphA4 aggregation was mediated by crosslinking an EphA4-specific scFv, using a secondary antibody. EphA4 antibody treatment of a pancreatic carcinoma cell line, ASPC1, resulted in multiple biological and biochemical consequences. First, cell adhesions to the extracellular matrix decreased (FIG. 1), which is significant since these types of adhesions are sites of intracellular signaling that promote cell growth, survival, migration and invasion (Burridge and Chrzanowska-Wodnicka, *Annu. Rev. Cell Dev. Biol.*, 12: 463, 1996; Parsons, *Curr. Opin. Cell Biol.*, 8:146, 1996). Secondly, EphA4 antibody-mediated aggregation inhibited anchorage-independent growth of ASPC1 cells, as measured using soft agar colonization assays (FIG. 3). Third, EphA4 activation resulted in the tyrosine phosphorylation of EphA4 and an EphA4-associated 75 kDa protein. Taken together, these data suggest that antibody-mediated activation of EphA4 initiates a signaling pathway that results in the reduced malignant potential of pancreatic carcinoma cells.

In another line of experiments, EphA4 upregulation promotes anchorage-independent growth of MCF-7 mammary carcinoma cell line to be less dependent on estrogen for growth. MCF-7 cells, which normally express very low levels of EphA4, were transfected, and stable expressors of EphA4 were isolated (EphA4-2 and EphA4-3). During soft agar assays with estrogen, MCF-7-EphA4 cells demonstrated a 2.4 fold increase in anchorage independent growth compared to a vector-transfected control (FIG. 4). However in the absence of estrogen, EphA4-expressing cells had a 8.5 fold increase in growth compared to the same controls. These data suggest that EphA4-overexpressing cells are less dependent on growth cues (such as matrix attachment and growth factors) than cells without EphA4. The results of these experiments also suggest that antibody-mediated aggregation of MCF-7-EphA4 cells can reverse the increase in malignant potential.

6.4. EphA4 RNA Levels are Increased in Pancreatic Tumor Tissue

EphA4 RNA levels were determined from patient samples to determine EphA4 expression in cancerous tissue. As demonstrated in FIG. 5, EphA4 RNA levels are increased in pancreatic tumor tissue relative to normal tissue. The bar labeled "Normal" (A) shows EphA4 RNA levels in pathologically normal pancreatic tissue from a 52-year old male patient. "Stage 4 Primary" (B) shows EphA4 RNA levels in pancreatic tissue displaying Stage 4A ductal pancreatic adenocarcinoma from the same 52-year old male patient from which the tissue in bar A was sampled. "Stage 2 Primary" (C) shows EphA4 RNA levels in pancreatic tissue displaying Stage 2A ductal pancreatic adenocarcinoma from a 72-year old male patient. "Met" (D) shows EphA4 RNA levels in lymph node tissue of a 71-year old female patient displaying Stage 2B metastatic pancreatic adenocarcinoma. "Met" (E) shows EphA4 RNA levels in omentum tissue of a 57-year old female patient displaying Stage 4 metastatic pancreatic adenocarcinoma. "Met" (F) shows EphA4 RNA levels in liver tissue of a 45-year old female patient displaying metastatic pancreatic adenocarcinoma. From these samples, it is evident that EphA4 expression is increased in cancerous and metastatic tissue relative to control tissue.

6.5. Treatment of Patients with Metastatic Cancer

A study is designed to assess pharmacokinetics and safety of monoclonal antibodies of the invention in patients with metastatic breast cancer. Patients currently receiving treatment are permitted to continue these medications.

Patients are administered a single IV dose of a monoclonal antibody of the invention and then, beginning 4 weeks later, are analyzed following administration of repeated weekly IV doses at the same dose over a period of 12 weeks. The safety of treatment with the monoclonal antibody of the invention is assessed as well as potential changes in disease activity over 26 weeks of IV dosing. Different groups of patients are treated and evaluated similarly but receive doses of 1 mg/kg, 2 mg/kg, 4 mg/kg, or 8 mg/kg.

Monoclonal antibodies of the invention are formulated at 5 mg/ml and 10 mg/ml for IV injection. A formulation of 80 mg/ml is required for repeated subcutaneous administration. The monoclonal antibodies of the invention are also formulated at 100 mg/ml for administration for the purposes of the study.

Changes are measured or determined by the progression of tumor growth.

6.6. Kinetic Analysis of EphA4 Antibodies

The surface plasmon resonance-based BIACORE™ assay is used to measure the $K_{off}$ rates of the monoclonal antibodies of the invention. IgG present in the hybridoma supernatant is used for measurement.

Immobilization of EphA4

EphA4 fusion protein is immobilized to a surface on a CM5 sensorchip using a standard amine (70 µl of a 1:1 mix of NHS/EDC) coupling chemistry. Briefly, a 400 nM solution of EphA4 fusion protein in 10 mM NaOAc, pH4, is then injected over the activated surface to a density of 1000-1100 RU's. Unused reactive esters are subsequently "capped" with a 70 µl injection of 1M Et-NH2. Similarly, an activated and "capped" control surface is prepared on the same sensor chip without protein to serve as a reference surface.

Binding Experiments

A 250 µl injection of each of the EphA4 hybridoma supernatants is made over both the EphA4 fusion protein and control surfaces, and the binding responses are recorded. These supernatants are used undiluted. Following each injection, at least 10 min. of dissociation phase data is collected. Purified EphA4 monoclonal antibody is prepared to serve as a positive control (at 1 µg, 5 µg and 25 µg per 250 µl of growth medium). A negative control monoclonal antibody that does not bind EphA4 is also prepared at 5 µg/250 µl growth medium. Control injections of growth medium across these surfaces are also made. Following each binding cycle, the EphA4 fusion protein surface is regenerated with a single 1 min. pulse (injection) of 1M NaCl-50 mM NaOH.

Data Evaluation

The binding data are corrected by subtracting out both artifactual noise (blank medium injections) and non-specific binding (control surface), in a technique known as "double-referencing." Thus the sensorgram overlays represent "net" binding curves. EphA4 antibodies have slow $K_{off}$ rates.

7. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

We claim:

1. An isolated monoclonal antibody that specifically binds human EphA4, and increases the phosphorylation of human EphA4.

2. The antibody of claim 1, wherein binding human EpbA4 inhibits cancer cell colony formation in soft agar or tubular network formation in a three-dimensional basement membrane or extracellular matrix preparation.

3. The antibody of claim 2, wherein said inhibition is caused by necrosis or apoptosis of cancer cells.

4. The antibody of claim 1, wherein binding human EphA4 reduces cancer cell colony formation in soft agar or tubular network formation in a three-dimensional basement membrane or extracellular matrix preparation.

5. The antibody of claim 4, wherein said reduction is caused by necrosis or apoptosis of cancer cells.

6. The antibody of claim 1, wherein binding human EphA4 occurs only when human EphA4 is not in a cell-cell contact or bound to EphrinA4 ligand.

7. The antibody of any one of claims 1, 2-6, or 3, wherein said antibody is humanized.

8. The antibody of any one of claims 1, 2-6, or 3, wherein said antibody is human.

9. An isolated cell line that produces an antibody of any one of claims 1, 2-6 or 3.

* * * * *

SEQUENCE LISTING

<160> NUMBER OF SEQ ID NOS: 32

<210> SEQ ID NO 1
<211> LENGTH: 60
<212> TYPE: DNA
<213> ORGANISM: Homo Sapiens
<220> FEATURE:
<223> OTHER INFORMATION: Protein III leader of antibody EA44

<400> SEQUENCE: 1
atgaaaaaat tattattcgc aattcctta gttgttcctt tctatgcggc ccagccggcc    60

<210> SEQ ID NO 2
<211> LENGTH: 20
<212> TYPE: PRT
<213> ORGANISM: Homo Sapiens
<220> FEATURE:
<223> OTHER INFORMATION: Protein III leader of antibody EA44

<400> SEQUENCE: 2

Met Lys Lys Leu Leu Phe Ala Ile Pro Leu Val Val Pro Phe Tyr Ala
 1               5                  10                  15

Ala Gln Pro Ala
          20

<210> SEQ ID NO 3
<211> LENGTH: 369
<212> TYPE: DNA
<213> ORGANISM: Homo Sapiens
<220> FEATURE:
<223> OTHER INFORMATION: VH sequence of antibody EA44

<400> SEQUENCE: 3
atggcacagg tgcagctgtt gcagtctgga gctgaggtga agaagcctgg ggcctcagtg    60
aaggttccct gcaaggcttc tggatacacc ttcactagct atgctatgag ttgggtgcga   120
caggcccctg gacaagggct tgagtggatg ggatggatca acaccaacac tgggaaccca   180
acgtatgccc agggcttcac aggacggttt gtcttctcct tggacacctc tgtcagcacg   240
gcatatctgc agatcagcag cctaaaggct gaggacactg ccgtgtatta ctgtgcgaga   300
gtccggacta cggtgtatgg ggacggtatg gacgtctggg gccaaggcac cctggtcacc   360
gtctcctca                                                            369

<210> SEQ ID NO 4
<211> LENGTH: 123
<212> TYPE: PRT
<213> ORGANISM: Homo Sapiens
<220> FEATURE:
<223> OTHER INFORMATION: VH sequence of antibody EA44

<400> SEQUENCE: 4

Met Ala Gln Val Gln Leu Leu Gln Ser Gly Ala Glu Val Lys Lys Pro
 1               5                  10                  15

Gly Ala Ser Val Lys Val Pro Cys Lys Ala Ser Gly Tyr Thr Phe Thr
             20                  25                  30

Ser Tyr Ala Met Ser Trp Val Arg Gln Ala Pro Gly Gln Gly Leu Glu
         35                  40                  45

Trp Met Gly Trp Ile Asn Thr Asn Thr Gly Asn Pro Tyr Ala Gln
     50                  55                  60

```
Gly Phe Thr Gly Arg Phe Val Phe Ser Leu Asp Thr Ser Val Ser Thr
 65                  70                  75                  80

Ala Tyr Leu Gln Ile Ser Ser Leu Lys Ala Glu Asp Thr Ala Val Tyr
                 85                  90                  95

Tyr Cys Ala Arg Val Arg Thr Val Tyr Gly Asp Gly Met Asp Val
            100                 105                 110

Trp Gly Gln Gly Thr Leu Val Thr Val Ser Ser
        115                 120
```

<210> SEQ ID NO 5
<211> LENGTH: 24
<212> TYPE: DNA
<213> ORGANISM: Homo Sapiens
<220> FEATURE:
<223> OTHER INFORMATION: Linker between VH and VL of antibody EA44

<400> SEQUENCE: 5

```
ggcggcggcg gcggtggcgg atcc                                           24
```

<210> SEQ ID NO 6
<211> LENGTH: 8
<212> TYPE: PRT
<213> ORGANISM: Homo Sapiens
<220> FEATURE:
<223> OTHER INFORMATION: Linker between VH and VL of antibody EA44

<400> SEQUENCE: 6

```
Gly Gly Gly Gly Gly Gly Gly Ser
 1               5
```

<210> SEQ ID NO 7
<211> LENGTH: 321
<212> TYPE: DNA
<213> ORGANISM: Homo Sapiens
<220> FEATURE:
<223> OTHER INFORMATION: VL sequence of antibody EA44

<400> SEQUENCE: 7

```
gaaattgtgc tgactcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagac   180
aggttcagcg ccagtgggtc tgggacggat ttcactctca ccatcagcag agtggaacct   240
gaagattttg cagtttatta ctgtcagcaa tatggtagtt catggacatt cggccaaggg   300
accaaggtgg aaatcaaacg t                                             321
```

<210> SEQ ID NO 8
<211> LENGTH: 107
<212> TYPE: PRT
<213> ORGANISM: Homo Sapiens
<220> FEATURE:
<223> OTHER INFORMATION: VL sequence of antibody EA44

<400> SEQUENCE: 8

```
Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Ile Pro Asp Arg Phe Ser Ala
 50                  55                  60

Ser Gly Ser Gly Thr Asp Phe Thr Leu Thr Ile Ser Arg Val Glu Pro
 65                  70                  75                  80

Glu Asp Phe Ala Val Tyr Tyr Cys Gln Gln Tyr Gly Ser Ser Trp Thr
                 85                  90                  95

Phe Gly Gln Gly Thr Lys Val Glu Ile Lys Arg
            100                 105
```

```
<210> SEQ ID NO 9
<211> LENGTH: 15
<212> TYPE: DNA
<213> ORGANISM: Homo Sapiens
<220> FEATURE:
<223> OTHER INFORMATION: Sfi I site

<400> SEQUENCE: 9
ggcctcgggg gcctg                                                15
```

```
<210> SEQ ID NO 10
<211> LENGTH: 5
<212> TYPE: PRT
<213> ORGANISM: Homo Sapiens
<220> FEATURE:
<223> OTHER INFORMATION: Sfi I site

<400> SEQUENCE: 10

Gly Leu Gly Gly Leu
 1               5
```

```
<210> SEQ ID NO 11
<211> LENGTH: 24
<212> TYPE: DNA
<213> ORGANISM: Homo Sapiens
<220> FEATURE:
<223> OTHER INFORMATION: FLAG-Tag

<400> SEQUENCE: 11
gactacaaag atgacgatga caaa                                      24
```

```
<210> SEQ ID NO 12
<211> LENGTH: 8
<212> TYPE: PRT
<213> ORGANISM: Homo Sapiens
<220> FEATURE:
<223> OTHER INFORMATION: FLAG-Tag

<400> SEQUENCE: 12

Asp Tyr Lys Asp Asp Asp Asp Lys
 1               5
```

```
<210> SEQ ID NO 13
<211> LENGTH: 18
<212> TYPE: DNA
<213> ORGANISM: Homo Sapiens
<220> FEATURE:
<223> OTHER INFORMATION: HIS-Tag

<400> SEQUENCE: 13
caccatcacc atcaccat                                             18
```

```
<210> SEQ ID NO 14
<211> LENGTH: 6
<212> TYPE: PRT
<213> ORGANISM: Homo Sapiens
```

-continued

<220> FEATURE:
<223> OTHER INFORMATION: HIS-Tag

<400> SEQUENCE: 14

His His His His His His
 1               5

<210> SEQ ID NO 15
<211> LENGTH: 837
<212> TYPE: DNA
<213> ORGANISM: Homo Sapiens
<220> FEATURE:
<223> OTHER INFORMATION: Precursor scFv (EA44) sequence

<400> SEQUENCE: 15

```
atgaaaaaat tattattcgc aattcccttta gttgttcctt tctatgcggc ccagccggcc      60
atggcacagg tgcagctgtt gcagtctgga gctgaggtga agaagcctgg ggcctcagtg     120
aaggttccct gcaaggcttc tggatacacc ttcactagct atgctatgag ttgggtgcga     180
caggcccctg gacaagggct tgagtggatg ggatggatca acaccaacac tgggaaccca     240
acgtatgccc agggcttcac aggacggttt gtcttctcct tggacacctc tgtcagcacg     300
gcatatctgc agatcagcag cctaaaggct gaggacactg ccgtgtatta ctgtgcgaga     360
gtccggacta cggtgtatgg ggacggtatg gacgtctggg gccaaggcac cctggtcacc     420
gtctcctcag gcggcggcgg cggtggcgga tccgaaattg tgctgactca gtctccagcc     480
accctgtctg tgtctccagg ggaaagagcc accctctcct gcagggccag tcagagtgtt     540
agcagcaact tagcctggta ccagcagaaa cctggccagg ctcccaggct cctcatctat     600
ggtgcatcca ccagggccac tggtatccca gacaggttca gcgccagtgg gtctgggacg     660
gatttcactc tcaccatcag cagagtggaa cctgaagatt ttgcagttta ttactgtcag     720
caatatggta gttcatggac attcggccaa gggaccaagg tggaaatcaa acgtggcctc     780
gggggcctgg actacaaaga tgacgatgac aaaggcgcac accatcacca tcaccat      837
```

<210> SEQ ID NO 16
<211> LENGTH: 279
<212> TYPE: PRT
<213> ORGANISM: Homo Sapiens
<220> FEATURE:
<223> OTHER INFORMATION: Precursor scFv (EA44) sequence

<400> SEQUENCE: 16

Met Lys Lys Leu Leu Phe Ala Ile Pro Leu Val Val Pro Phe Tyr Ala
 1               5                  10                  15

Ala Gln Pro Ala Met Ala Gln Val Gln Leu Leu Gln Ser Gly Ala Glu
            20                  25                  30

Val Lys Lys Pro Gly Ala Ser Val Lys Val Pro Cys Lys Ala Ser Gly
        35                  40                  45

Tyr Thr Phe Thr Ser Tyr Ala Met Ser Trp Val Arg Gln Ala Pro Gly
    50                  55                  60

Gln Gly Leu Glu Trp Met Gly Trp Ile Asn Thr Asn Thr Gly Asn Pro
65                  70                  75                  80

Thr Tyr Ala Gln Gly Phe Thr Gly Arg Phe Val Phe Ser Leu Asp Thr
                85                  90                  95

Ser Val Ser Thr Ala Tyr Leu Gln Ile Ser Ser Leu Lys Ala Glu Asp
            100                 105                 110

Thr Ala Val Tyr Tyr Cys Ala Arg Val Arg Thr Thr Val Tyr Gly Asp
        115                 120                 125

```
Gly Met Asp Val Trp Gly Gln Gly Thr Leu Val Thr Val Ser Ser Gly
    130                 135                 140
Gly Gly Gly Gly Gly Ser Glu Ile Val Leu Thr Gln Ser Pro Ala
145                 150                 155                 160
Thr Leu Ser Val Ser Pro Gly Glu Arg Ala Thr Leu Ser Cys Arg Ala
                165                 170                 175
Ser Gln Ser Val Ser Ser Asn Leu Ala Trp Tyr Gln Gln Lys Pro Gly
            180                 185                 190
Gln Ala Pro Arg Leu Leu Ile Tyr Gly Ala Ser Thr Arg Ala Thr Gly
        195                 200                 205
Ile Pro Asp Arg Phe Ser Ala Ser Gly Ser Gly Thr Asp Phe Thr Leu
    210                 215                 220
Thr Ile Ser Arg Val Glu Pro Glu Asp Phe Ala Val Tyr Tyr Cys Gln
225                 230                 235                 240
Gln Tyr Gly Ser Ser Trp Thr Phe Gly Gln Gly Thr Lys Val Glu Ile
                245                 250                 255
Lys Arg Gly Leu Gly Gly Leu Asp Tyr Lys Asp Asp Asp Asp Lys Gly
            260                 265                 270
Ala His His His His His His
        275
```

<210> SEQ ID NO 17
<211> LENGTH: 777
<212> TYPE: DNA
<213> ORGANISM: Homo Sapiens
<220> FEATURE:
<223> OTHER INFORMATION: Mature scFv (EA44) sequence with FLAG & HIS
      Tags

<400> SEQUENCE: 17

```
atggcacagg tgcagctgtt gcagtctgga gctgaggtga agaagcctgg ggcctcagtg    60
aaggttccct gcaaggcttc tggatacacc ttcactagct atgctatgag ttgggtgcga   120
caggcccctg gacaagggct tgagtggatg ggatggatca acaccaacac tgggaaccca   180
acgtatgccc agggcttcac aggacggttt gtcttctcct tggacacctc tgtcagcacg   240
gcatatctgc agatcagcag cctaaaggct gaggacactg ccgtgtatta ctgtgcgaga   300
gtccggacta cggtgtatgg ggacggtatg gacgtctggg gccaaggcac cctggtcacc   360
gtctcctcag gcggcggcgg cggtggcgga tccgaaattg tgctgactca gtctccagcc   420
accctgtctg tgtctccagg ggaaagagcc accctctcct gcagggccag tcagagtgtt   480
agcagcaact tagcctggta ccagcagaaa cctggccagg ctcccaggct cctcatctat   540
ggtgcatcca ccagggccac tggtatccca gacaggttca gcgccagtgg gtctgggacg   600
gatttcactc tcaccatcag cagagtggaa cctgaagatt ttgcagttta ttactgtcag   660
caatatggta gttcatggac attcggccaa gggaccaagg tggaaatcaa acgtggcctc   720 ggggggcctgg actacaaaga tgacgatgac aaaggcgcac accatcacca tcaccat    777
```

<210> SEQ ID NO 18
<211> LENGTH: 259
<212> TYPE: PRT
<213> ORGANISM: Homo Sapiens
<220> FEATURE:
<223> OTHER INFORMATION: Mature scFv (EA44) sequence with FLAG & HIS
      Tags

```
<400> SEQUENCE: 18

Met Ala Gln Val Gln Leu Leu Gln Ser Gly Ala Glu Val Lys Lys Pro
 1               5                  10                  15

Gly Ala Ser Val Lys Val Pro Cys Lys Ala Ser Gly Tyr Thr Phe Thr
             20                  25                  30

Ser Tyr Ala Met Ser Trp Val Arg Gln Ala Pro Gly Gln Gly Leu Glu
         35                  40                  45

Trp Met Gly Trp Ile Asn Thr Asn Thr Gly Asn Pro Thr Tyr Ala Gln
 50                  55                  60

Gly Phe Thr Gly Arg Phe Val Phe Ser Leu Asp Thr Ser Val Ser Thr
 65                  70                  75                  80

Ala Tyr Leu Gln Ile Ser Ser Leu Lys Ala Glu Asp Thr Ala Val Tyr
                 85                  90                  95

Tyr Cys Ala Arg Val Arg Thr Thr Val Tyr Gly Asp Gly Met Asp Val
            100                 105                 110

Trp Gly Gln Gly Thr Leu Val Thr Val Ser Ser Gly Gly Gly Gly
            115                 120                 125

Gly Gly Ser Glu Ile Val Leu Thr Gln Ser Pro Ala Thr Leu Ser Val
        130                 135                 140

Ser Pro Gly Glu Arg Ala Thr Leu Ser Cys Arg Ala Ser Gln Ser Val
145                 150                 155                 160

Ser Ser Asn Leu Ala Trp Tyr Gln Gln Lys Pro Gly Gln Ala Pro Arg
                165                 170                 175

Leu Leu Ile Tyr Gly Ala Ser Thr Arg Ala Thr Gly Ile Pro Asp Arg
            180                 185                 190

Phe Ser Ala Ser Gly Ser Gly Thr Asp Phe Thr Leu Thr Ile Ser Arg
        195                 200                 205

Val Glu Pro Glu Asp Phe Ala Val Tyr Tyr Cys Gln Gln Tyr Gly Ser
    210                 215                 220

Ser Trp Thr Phe Gly Gln Gly Thr Lys Val Glu Ile Lys Arg Gly Leu
225                 230                 235                 240

Gly Gly Leu Asp Tyr Lys Asp Asp Asp Lys Gly Ala His His His
                245                 250                 255

His His His

<210> SEQ ID NO 19
<211> LENGTH: 714
<212> TYPE: DNA
<213> ORGANISM: Homo Sapiens
<220> FEATURE:
<223> OTHER INFORMATION: Mature scFv (EA44) sequence without FLAG & HIS
      Tags

<400> SEQUENCE: 19
atggcacagg tgcagctgtt gcagtctgga gctgaggtga agaagcctgg ggcctcagtg    60
aaggttccct gcaaggcttc tggatacacc ttcactagct atgctatgag ttgggtgcga   120
caggcccctg acaagggct tgagtggatg ggatggatca acaccaacac tgggaaccca   180
acgtatgccc agggcttcac aggacggttt gtcttctcct tggacacctc tgtcagcacg   240
gcatatctgc agatcagcag cctaaaggct gaggacactg ccgtgtatta ctgtgcgaga   300
gtccggacta cggtgtatgg ggacggtatg gacgtctggg gccaaggcac cctggtcacc   360
gtctcctcag gcggcggcgg cggtggcgga tccgaaattg tgctgactca gtctccagcc   420
accctgtctg tgtctccagg ggaaagagcc accctctcct gcagggccag tcagagtgtt   480
```

-continued

```
agcagcaact tagcctggta ccagcagaaa cctggccagg ctcccaggct cctcatctat      540
ggtgcatcca ccagggccac tggtatccca gacaggttca cgccagtgg gtctgggacg      600 gatttcactc tcaccatcag cagagtggaa cctgaagatt ttgcagttta ttactgtcag     660
caatatggta gttcatggac attcggccaa gggaccaagg tggaaatcaa acgt          714
```

<210> SEQ ID NO 20
<211> LENGTH: 238
<212> TYPE: PRT
<213> ORGANISM: Homo Sapiens
<220> FEATURE:
<223> OTHER INFORMATION: Mature scFv (EA44) sequence without FLAG & HIS
      Tags

<400> SEQUENCE: 20

```
Met Ala Gln Val Gln Leu Leu Gln Ser Gly Ala Glu Val Lys Lys Pro
1               5                   10                  15

Gly Ala Ser Val Lys Val Pro Cys Lys Ala Ser Gly Tyr Thr Phe Thr
            20                  25                  30

Ser Tyr Ala Met Ser Trp Val Arg Gln Ala Pro Gly Gln Gly Leu Glu
        35                  40                  45

Trp Met Gly Trp Ile Asn Thr Asn Thr Gly Asn Pro Thr Tyr Ala Gln
    50                  55                  60

Gly Phe Thr Gly Arg Phe Val Phe Ser Leu Asp Thr Ser Val Ser Thr
65                  70                  75                  80

Ala Tyr Leu Gln Ile Ser Ser Leu Lys Ala Glu Asp Thr Ala Val Tyr
                85                  90                  95

Tyr Cys Ala Arg Val Arg Thr Thr Val Tyr Gly Asp Gly Met Asp Val
            100                 105                 110

Trp Gly Gln Gly Thr Leu Val Thr Val Ser Ser Gly Gly Gly Gly Gly
        115                 120                 125

Gly Gly Ser Glu Ile Val Leu Thr Gln Ser Pro Ala Thr Leu Ser Val
    130                 135                 140

Ser Pro Gly Glu Arg Ala Thr Leu Ser Cys Arg Ala Ser Gln Ser Val
145                 150                 155                 160

Ser Ser Asn Leu Ala Trp Tyr Gln Gln Lys Pro Gly Gln Ala Pro Arg
                165                 170                 175

Leu Leu Ile Tyr Gly Ala Ser Thr Arg Ala Thr Gly Ile Pro Asp Arg
            180                 185                 190

Phe Ser Ala Ser Gly Ser Gly Thr Asp Phe Thr Leu Thr Ile Ser Arg
        195                 200                 205

Val Glu Pro Glu Asp Phe Ala Val Tyr Tyr Cys Gln Gln Tyr Gly Ser
    210                 215                 220

Ser Trp Thr Phe Gly Gln Gly Thr Lys Val Glu Ile Lys Arg
225                 230                 235
```

<210> SEQ ID NO 21
<211> LENGTH: 15
<212> TYPE: DNA
<213> ORGANISM: Homo sapiens
<220> FEATURE:
<223> OTHER INFORMATION: CDR1 of VH region of EA44

<400> SEQUENCE: 21

```
agctatgcta tgagt                                                      15
```

```
<210> SEQ ID NO 22
<211> LENGTH: 5
<212> TYPE: PRT
<213> ORGANISM: Homo sapiens
<220> FEATURE:
<223> OTHER INFORMATION: CDR1 of VH region of EA44

<400> SEQUENCE: 22

Ser Tyr Ala Met Ser
 1               5

<210> SEQ ID NO 23
<211> LENGTH: 51
<212> TYPE: DNA
<213> ORGANISM: Homo sapiens
<220> FEATURE:
<223> OTHER INFORMATION: CDR2 of VH region of EA44

<400> SEQUENCE: 23
tggatcaaca ccaacactgg gaacccaacg tatgcccagg gcttcacagg a            51

<210> SEQ ID NO 24
<211> LENGTH: 17
<212> TYPE: PRT
<213> ORGANISM: Homo sapiens
<220> FEATURE:
<223> OTHER INFORMATION: CDR2 of VH region of EA44

<400> SEQUENCE: 24

Trp Ile Asn Thr Asn Thr Gly Asn Pro Thr Tyr Ala Gln Gly Phe Thr
 1               5                  10                  15

Gly

<210> SEQ ID NO 25
<211> LENGTH: 36
<212> TYPE: DNA
<213> ORGANISM: Homo sapiens
<220> FEATURE:
<223> OTHER INFORMATION: CDR3 of VH region of EA44

<400> SEQUENCE: 25
gtccggacta cggtgtatgg ggacggtatg gacgtc                              36

<210> SEQ ID NO 26
<211> LENGTH: 12
<212> TYPE: PRT
<213> ORGANISM: Homo sapiens
<220> FEATURE:
<223> OTHER INFORMATION: CDR3 of VH region of EA44

<400> SEQUENCE: 26

Val Arg Thr Thr Val Tyr Gly Asp Gly Met Asp Val
 1               5                  10

<210> SEQ ID NO 27
<211> LENGTH: 33
<212> TYPE: DNA
<213> ORGANISM: Homo sapiens
<220> FEATURE:
<223> OTHER INFORMATION: CDR1 of VL region of EA44

<400> SEQUENCE: 27
agggccagtc agagtgttag cagcaactta gcc                                 33
```

```
<210> SEQ ID NO 28
<211> LENGTH: 11
<212> TYPE: PRT
<213> ORGANISM: Homo sapiens
<220> FEATURE:
<223> OTHER INFORMATION: CDR1 of VL region of EA44

<400> SEQUENCE: 28

Arg Ala Ser Gln Ser Val Ser Ser Asn Leu Ala
 1               5                  10

<210> SEQ ID NO 29
<211> LENGTH: 21
<212> TYPE: DNA
<213> ORGANISM: Homo sapiens
<220> FEATURE:
<223> OTHER INFORMATION: CDR2 of VL region of EA44

<400> SEQUENCE: 29
ggtgcatcca ccagggccac t                                          21

<210> SEQ ID NO 30
<211> LENGTH: 7
<212> TYPE: PRT
<213> ORGANISM: Homo sapiens
<220> FEATURE:
<223> OTHER INFORMATION: CDR2 of VL region of EA44

<400> SEQUENCE: 30

Gly Ala Ser Thr Arg Ala Thr
 1               5

<210> SEQ ID NO 31
<211> LENGTH: 24
<212> TYPE: DNA
<213> ORGANISM: Homo sapiens
<220> FEATURE:
<223> OTHER INFORMATION: CDR3 of VL region of EA44

<400> SEQUENCE: 31
cagcaatatg gtagttcatg gaca                                       24

<210> SEQ ID NO 32
<211> LENGTH: 8
<212> TYPE: PRT
<213> ORGANISM: Homo sapiens
<220> FEATURE:
<223> OTHER INFORMATION: CDR3 of VL region of EA44

<400> SEQUENCE: 32

Gln Gln Tyr Gly Ser Ser Trp Thr
 1               5
```